United States Patent [19]

Rupniak

[11] Patent Number: 6,090,819

[45] Date of Patent: Jul. 18, 2000

[54] USE OF NK-1 RECEPTOR ANTAGONISTS FOR TREATING MANIA

[75] Inventor: Nadia Melanie Rupniak, Bishops Stortford, United Kingdom

[73] Assignee: Merck Sharp & Dohme, Ltd., Hoddesdon, United Kingdom

[21] Appl. No.: 09/362,277

[22] Filed: Jul. 27, 1999

Related U.S. Application Data

[62] Division of application No. 08/982,194, Dec. 1, 1997, Pat. No. 5,952,330.

[30] Foreign Application Priority Data

Aug. 4, 1997 [GB] United Kingdom ............... 9716463

[51] Int. Cl.⁷ .................................................. A61K 31/438
[52] U.S. Cl. ............................................................ 514/278
[58] Field of Search ............................................ 514/278

[56] References Cited

U.S. PATENT DOCUMENTS

| | | | |
|---|---|---|---|
| 5,162,339 | 11/1992 | Lowe, III | 514/305 |
| 5,538,982 | 7/1996 | Hagan et al. | 514/305 |
| 5,612,337 | 3/1997 | Baker et al. | 514/236.2 |
| 5,719,147 | 2/1998 | Dom et al. | 514/227.5 |
| 5,952,315 | 9/1999 | Baker et al. | 514/90 |

FOREIGN PATENT DOCUMENTS

| | | |
|---|---|---|
| 0 436 334 A2 | 7/1991 | European Pat. Off. . |
| 0 499 313 A1 | 8/1992 | European Pat. Off. . |
| WO 93/14084 | 7/1993 | WIPO . |
| WO 95/08549 | 3/1995 | WIPO . |
| WO 96/24353 | 8/1996 | WIPO . |
| WO 97/45119 | 12/1997 | WIPO . |
| WO 97/49710 | 12/1997 | WIPO . |

OTHER PUBLICATIONS

Aguiar, M., et al., *Physiology & Behavior*, 1996, 60 (4) 1183–1186.
Barden, N., et al., *J. Neurochem.*, 1983, 41, 834–840.
Brodin, E., et al., *Neuropharmacology*, 1987, 26 (6) 581–590.
Brodin, E., et al., *Neuropeptides*, 1994, 26, 253–260.
Culman, J., et al., *J. Physiol. Pharmacol.*, 1995, 73, 885–891.
Cutler, et al., J Psychopharmacol, 1994, 8 A22, 87.
Elliott, P. J., *Exp. Brain Res. UK*, 1988, 73, 354–356.
*F–D–C Reports—Prescription Pharmaceuticals and Biotechnology*, Dec. 8, 1997, 59 (49), 10.
File, S. E., *Pharm. Biochem. Behavior*, 1997, 58, 3, 747–752.
Lowe, J., et al., *Drug News Perspect*, 1992, 5 (4), 223.
Malek–Ahmadi, *Neuroscience and Behavioral Reviews*, 1992, 16, 365–359.
Rimon, R., et al., *Biological Psychiatry*, 1984, 19 (4), 509–516.
Roccon, et al., *Pharmacological Research*, 1995, 31, 191.
Shaikh, M., et al., *Brain Research*, 1993, 625, 283–294.
Shirayama, Y., et al., *Brain Research*, 1996, 739, 70–78.
Siegel, R., et al., *Neurochem. Int.*, 1984, 6 (6), 783–789.
Siegel, A., et al., *Aggressive Behavior*, 1995, 21, 49–62.
Teixeira, R., et al., *European J. Pharm.*, 1996, 311, 7–14.
Vassout, et al., *Neuropeptides*, 1994, 26 (Suppl. 1), 38.

*Primary Examiner*—Phyllis G. Spivack
*Attorney, Agent, or Firm*—J. Eric Thies; David L. Rose

[57] ABSTRACT

A method for the treatment or prevention of mania or hypomania is disclosed comprising administering 3-[2-cyclopropoxy-5-(trifluoromethoxy)phenyl]-6-phenyl-1-oxa-7-aza-spiro[4.5]decane.

2 Claims, No Drawings

USE OF NK-1 RECEPTOR ANTAGONISTS FOR TREATING MANIA

The enclosed comprises a division of prior application Ser. No. 08/982,194, as filed on Dec. 1, 1997, now U.S. Pat. No. 5,952,330.

This invention relates to the treatment or prevention of mania by the administration of a NK-1 receptor antagonist.

A Manic Episode is defined by a distinct period during which there is an abnormally and persistently elevated, expansive, or irritable mood. This period of abnormal mood must last at least 1 week (or less if hospitalization is required). The mood disturbance must be accompanied by at least three additional symptoms from a list that includes inflated self-esteem or grandiosity, decreased need for sleep, pressure of speech, flight of ideas, distractibility, increased involvement in goal-directed activities or psychomotor agitation, and excessive involvement in pleasurable activities with a high potential of painful consequences. If the mood is irritable (rather than elevated or expansive), at least four of the above symptoms must be present. The disturbance must be sufficiently severe to cause marked impairment in social or occupational functioning or to require hospitalization, or it is characterised by the presence of psychotic features. The episode must not be due to the direct physiological effects of a drug of abuse, a medication, other somatic treatments for depression (e.g., electroconvulsive therapy or light therapy) or toxin exposure. The episode must also not be due to the direct physiological effects of a general medical condition (e.g., multiple sclerosis, brain tumour). (Diagnostic and Statistical Manual of Mental Disorders, Fourth Edition, American Psychiatric Association, 1994).

The elevated mood of a Manic Episode may be described as euphoric, unusually good, cheerful, or high. Although the person's mood may initially have an infectious quality for the uninvolved observer, it is recognized as excessive by those who know the person well. The expansive quality of the mood is characterised by unceasing and indiscriminate enthusiasm for interpersonal, sexual or occupational interactions. Although the elevated mood is considered the prototypical symptom, the predominant mood disturbance may be irritability, particularly when the person's wishes are thwarted. Lability of mood (e.g. the alternation between euphoria and irritability) is frequently seen.

Treatment of mania is with drugs and psychological management. Typically, drugs such as haloperidol or chlorpromazine may be used to control symptoms. After more than one episode of mania, lithium carbonate is often prescribed. Drugs such as haloperidol and chlorpromazine are typically associated with a number of side-effects, including extrapyramidal symptoms, acute dystonias, tardive dyskinesias, akathesia, tremor, tachycardia, drowsiness, confusion, postural hypotension, blurring of vision, precipitation of glaucoma, dry mouth, constipation urinary hesitance and impaired sexual function. The therapeutic index of lithium is low and close control of plasma concentrations is required for its safe clinical application. Side-effects of lithium include tremor, nausea, diarrhoea, thirst and polyuria.

Neurokinin 1 (NK-1; substance P) receptor antagonists are being developed for the treatment of a number of physiological disorders associated with an excess or imbalance of tachykinins, and in particular substance P. Examples of conditions in which substance P has been implicated include disorders of the central nervous system such as anxiety, depression and psychosis (see, for instance, International (PCT) patent specification Nos. WO 95/16679, WO 95/18124 and WO 95/23798).

In view of the short-comings of existing agents for the treatment of mania, there is a need for new, safe and effective treatment of mania.

The present invention accordingly provides the use of a NK-1 receptor antagonist for the manufacture of a medicament for the treatment or prevention of mania.

The present invention also provides a method for the treatment or prevention of mania, which method comprises administration to a patient in need of such treatment of an effective amount of a NK-1 receptor antagonist.

In a further aspect of the present invention, there is provided a pharmaceutical composition for the treatment or prevention of mania comprising a NK-1 receptor antagonist, together with at least one pharmaceutically acceptable carrier or excipient.

Included within the scope of the present invention is the use of NK-1 receptor antagonists in the treatment or prevention of hypomania. A hypomanic episode is distinguished from a manic episode in that it is not severe enough to cause marked impairment in social and occupational functioning or to require hospitalisation, and there are no psychotic features.

Thus, in a further aspect of the present invention, there is provided the use of a NK-1 receptor antagonist for the manufacture of a medicament for the treatment or prevention of hypomania.

The present invention also provides a method for the treatment or prevention of hypomania, which method comprises adminstration to a patient in need of such treatment of an effective amount of a NK-1 receptor antagonist.

In a further aspect of the present invention, there is provided a pharmaceutical composition for the treatment or prevention of hypomania comprising a NK-1 receptor antagonist, together with at least one pharmaceutically acceptable carrier or excipient.

It will be appreciated that a combination of a conventional antipsychotic drug with a NK-1 receptor antagonist may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimising the risk of adverse side-effects. A yet further advantage of such a combination is that, due to the action of the NK-1 receptor antagonist, adverse side-effects caused by the antipsychotic agent such as acute dystonias, dyskinesias, akathesia and tremor may be reduced or prevented. Thus, according to a further aspect of the present invention there is provided the use of a NK-1 receptor antagonist and an antipsychotic agent for the manufacture of a medicament for the treatment or prevention of mania.

The present invention also provides-a method for the treatment or prevention of mania, which method comprises administration to a patient in need of such treatment of an amount of a NK-1 receptor antagonist and an amount of an antipsychotic agent, such that together they give effective relief.

In a further aspect of the present invention-, there is provided a pharmaceutical composition comprising a NK-1 receptor antagonist and an antipsychotic agent, together with at least one pharmaceutically acceptable carrier or excipient.

It will be appreciated that the NK-1 receptor antagonist and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a NK-1 receptor antagonist and an antipsychotic agent as a combined preparation for simultaneous, separate or sequential use in the treatment or prevention of mania.

It will be appreciated that when using a combination of the present invention, the NK-1 receptor antagonist and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the NK-1 receptor antagonist may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of NK-1 receptor antagonists in combination with an antipsychotic agent in the treatment or prevention of hypomania.

As used herein, the term "treatment" refers both to the treatment and to the prevention or prophylactic therapy of mania or hypomania.

NK-1 receptor antagonists of use in the present invention are described in published European Patent Specification Nos. 0 360 390, 0 394 989, 0 429 366, 0 443 132, 0 482 539, 0 512 901, 0 512 902, 0 514 273, 0 514 275, 0 517 589, 0 520 555, 0 522 808, 0 528 495, 0 532 456, 0 533 280, 0 536 817, 0 545 478, 0 577 394, 0 590 152, 0 599 538, 0 610 793, 0 634 402, 0 686 629, 0 693 489, 0 694 535, 0 699 655, 0 699 674, 0 707 006, 0 708 101, 0 714 891, 0 723 959, 0 733 632 and 0 776 893; and in International Patent Specification Nos. 90/05525, 90/05729, 91/09844, 91/18899, 92/01688, 92/06079, 92/12151, 92/15585, 92/17449, 92/20661, 92/20676, 92/21677, 93/00330, 93/00331, 93/01159, 93/01165, 93/01169, 93/01170, 93/06099, 93/09116, 93/10073, 93/14113, 93/18023, 93/19064, 93/21155, 9321181, 93/23380, 93/24465, 94/01402, 94/02461, 94/03429, 94/03445, 94/04494, 94/04496, 94/05625, 94/07843, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 96/22525, 95/23798, 95/26338, 95/28418, 95/30674, 95/30687, 96/05193,;96/ 05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Specification Nos. 2 266 529, 2 268 931, 2 269 170, 2 269 590, 2 271 774, 2 292 144, 2 293 168, 2 293 169, and 2 302 689.

Suitable antipsychotic agents of use in combination with a NK-1 receptor antagonist include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a NK-1 receptor antagonist may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

Particularly preferred NK-1 receptor antagonists are those described in European Patent Specification No. 0 577 394, i.e. compounds of formula (I):

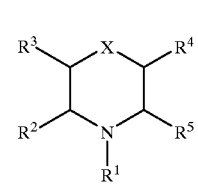

(1)

or a pharmaceutically acceptable salt thereof, wherein:
$R^1$ is selected from the group consisting of:
(1) hydrogen;
(2) $C_{1-6}$alkyl, unsubstituted or substituted with one or more of the substituents selected from:
 (a) hydroxy,
 (b) oxo,
 (c) $C_{1-6}$alkoxy,
 (d) phenyl-$C_{1-3}$alkoxy,
 (e) phenyl,
 (f) —CN,
 (g) halo,
 (h) —$NR^9R^{10}$, wherein $R^9$ and $R^{10}$ are independently selected from:
  (i) hydrogen,
  (ii) $C_{1-6}$alkyl,
  (iii) hydroxy-$C_{1-6}$alkyl, and
  (iv) phenyl,
 (i) —$NR^9COR^{10}$, wherein $R^9$ and $R^{10}$ are as defined above,
 (j) —$NR^9CO_2R^{10}$, wherein $R^9$ and $R^{10}$ are as defined above,
 (k) —$CONR^9R^{10}$, wherein $R^9$ and $R^{10}$ are as defined above,
 (l) —$COR^9$, wherein $R^9$ is as defined above,
 (m) —$CO_2R^9$, wherein $R^9$ is as defined above,
 (n) heterocycle, wherein the heterocycle is selected from the group consisting of:
  (A) benzimidazolyl,
  (B) benzofuranyl,
  (C) benzthiophenyl,
  (D) benzoxazolyl,
  (E) furanyl,
  (F) imidazolyl,
  (G) indolyl, (H) isoxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1,4-dioxanyl,
(Y) hexahydroazepinyl,
(Z) oxanyl,
(AA) piperazinyl,
(AB) piperidinyl,
(AC) pyrrolidinyl,
(AD) tetrahydrofuranyl, and
(AE) tetrahydrothienyl, and wherein the heterocylcle is unsubstituted or substituted with one or more substituent(s) selected from:
(i) $C_{1-6}$alkyl, unsubstituted or substituted with halo, —$CF_3$, —$OCH_3$, or phenyl,
(ii) $C_{1-6}$alkoxy,
(iii) oxo,
(iv) hydroxy,
(v) thioxo,
(vi) —$SR^9$, wherein $R^9$ is as defined above,
(vii) halo,
(viii) cyano,
(ix) phenyl,
(x) trifluoromethyl,
(xi) —$(CH_2)_m$—$NR^9R^{10}$, wherein m is 0, 1 or 2, and $R^9$ and $R^{10}$ are as defined above,
(xii) —$NR^9COR^{10}$, wherein $R^9$ and $R^{10}$ are as defined above,
(xiii) —$CONR^9R^{10}$, wherein $R^9$ and $R^{10}$ are as defined above,
(xiv) —$CO_2R^9$, wherein $R^9$ is as defined above, and
(xv) —$(CH_2)_m$—$OR^9$, wherein m and $R^9$ are as defined above;

(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above,
(k) heterocycle, wherein the heterocycle is as defined above;

(4) $C_{2-6}$alkynyl;
(5) phenyl, unsubstitued or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9R^{10}$, wherein m, $R^9$ and $R^{10}$ are as defined above,
(j) —$NR^9COR^{10}$, wherein $R^9$ and $R^{10}$ are as defined above,
(k) —$NR^9CO_2R^{10}$, wherein $R^9$ and $R^{10}$ are as defined above, (l) —$CONR^9R^{10}$, wherein $R^9$ and $R^{10}$ are as defined above,
(m) —$CO_2NR^9R^{10}$, wherein $R^9$ and $R^{10}$ are as defined above,
(n) —$COR^9$, wherein $R^9$ is as defined above,
(o) —$CO_2R^9$, wherein $R^9$ is as defined above;

$R^2$ and $R^3$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are independently elected from:
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above, and
(m) —$CO_2R^9$, wherein $R^9$ is as defined above;

(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$ wherein $R^9$ and $R^{10}$ are as defined above,
(i) —$COR^9$, wherein $R^9$ is as defined above,
(j) —$CO_2R^9$, wherein $R^9$ is as defined above;

(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9R^{10}$, wherein m, $R^9$ and $R^{10}$ are as defined above,
(j) —$NR^9COR^{10}$, wherein $R^9$ and $R^{10}$ are as defined above, (k) —NR⁹CO₂R¹⁰, wherein R⁹ and R¹⁰ are as defined above,
(l) —CONR⁹R¹⁰, wherein R⁹ and R¹⁰ are as defined above,
(m) —CO₂NR⁹R¹⁰, wherein R⁹ and R¹⁰ are as defined above,
(n) —COR⁹, wherein R⁹ is as defined above,
(o) —CO₂R⁹, wherein R⁹ is as defined above;

and the groups R¹ and R² may be joined together to form a heterocyclic ring selected from the group consisting of:
(a) pyrrolidinyl,
(b) piperidinyl,
(c) pyrrolyl,
(d) pyridinyl,
(e) imidazolyl,
(f) oxazolyl, and
(g) thiazolyl, and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —NR⁹R¹⁰, wherein R⁹ and R¹⁰ are as defined above,
(v) halo, and
(vi) trifluoromethyl;

and the groups R² and R³ may be joined together to form a carbocyclic ring selected from the group consisting of:
(a) cyclopentyl,
(b) cyclohexyl,
(c) phenyl, and wherein the carbocyclic ring is unsubstituted or substituted with one or more substituents selected from:
(i) $C_{1-6}$alkyl,
(ii) $C_{1-6}$alkoxy,
(iii) —NR⁹R¹⁰, wherein R⁹ and R¹⁰ are as defined above,
(iv) halo, and
(v) trifluoromethyl;

and the groups R² and R³ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl, and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —NR⁹R¹⁰, wherein R⁹ and R¹⁰ are as defined above,
(v) halo, and
(vi) trifluoromethyl;

X is selected from the group consisting of:
(1) —O—,
(2) —S—,
(3) —SO—, and
(4) —SO₂—;

R⁴ is selected from the group consisting of:

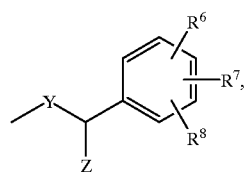

(1)

(2) —Y—$C_{1-8}$alkyl, wherein alkyl is unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —NR⁹R¹⁰, wherein R⁹ and R¹⁰ are as defined above,
(i) —NR⁹COR¹⁰, wherein R⁹ and R¹⁰ are as defined above,
(j) —NR⁹CO₂R¹⁰, wherein R⁹ and R¹⁰ are as defined above,
(k) —CONR⁹R¹⁰, wherein R⁹ and R¹⁰ are as defined above,
(l) —COR⁹, wherein R⁹ is as defined above,
(m) —CO₂R⁹, wherein R⁹ is as defined above;

(3) —Y—$C_{2-6}$alkenyl, wherein the alkenyl is unsubstituted or substituted with one or more of the substituent (s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —CONR⁹R¹⁰, wherein R⁹ and R¹⁰ are as defined above,
(i) —COR⁹, wherein R⁹ is as defined above,
(j) —CO₂R⁹, wherein R⁹ is as defined above, (4) —O(CO)-phenyl, wherein the phenyl is unsubstituted or substituted with one or more of R⁶, R⁷ and R⁸;

R⁵ is selected from the group consisting of:
(1) phenyl, unsubstituted or substituted with one or more of R¹¹, R¹² and R¹³;
(2) $C_{1-8}$alkyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —NR⁹R¹⁰, wherein R⁹ and R¹⁰ are as defined above,
(i) —NR⁹COR¹⁰, wherein R⁹ and R¹⁰ are as defined above,
(j) —NR⁹CO₂R¹⁰, wherein R⁹ and R¹⁰ are as defined above, (k) —CONR$^9$R$^{10}$, wherein R$^9$ and R$^{10}$ are as defined above,
(l) —COR$^9$, wherein R$^9$ is as defined above,
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl-C$_{1-3}$alkoxy,
(e) phenyl,
(fi) —CN,
(g) halo,
(h) —CONR$^9$R$^{10}$, wherein R$^9$ and R$^{10}$ are as defined above,
(i) —COR$^9$, wherein R$^9$ is as defined above,
(j) —CO$_2$R$^9$, wherein R$^9$ is as defined above;
(4) heterocycle, wherein the heterocycle is as defined above;
R$^6$, R$^7$ and R$^8$ are independently selected from the group consisting of:
(1) hydrogen;
(2) C$_{1-6}$alkyl, unsubstituted or substituted with one or more of the substituents selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) C$_{2-6}$alkynyl;
(5) phenyl, unsubstituted or substituted with one or more of the substituent(s) selected from:
(a) hydroxy,
(b) C$_{1-6}$alkoxy,
(c) C$_{1-6}$alkyl,
(d) C$_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above;
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or C$_{1-5}$alkyl,
(11) —SOR$^{14}$, wherein R$^{14}$ is as defined above,
(12) —SO$_2$R$^{14}$, wherein R$^{14}$ is as defined above,
(13) NR$^9$COR$^{10}$, wherein R$^9$ and R$^{10}$ are as defined above,
(14) CONR$^9$COR$^{10}$, wherein R$^9$ and R$^{10}$ are as defined above,
(15) NR$^9$R$^{10}$, wherein R$^9$ and R$^{10}$ are as defined above,
(16) NR$^9$CO$_2$R$^{10}$, wherein R$^9$ and R$^{10}$ are as defined above,
(17) hydroxy,
(18) C$_{1-6}$alkoxy,
(19) COR$^9$, wherein R$^9$ is as defined above,
(20) CO$_2$R$^9$, wherein R$^9$ is as defined above,
R$^{11}$, R$^{12}$ and R$^{13}$ are independently selected from the definitions of R$^6$, R$^7$ and R$^8$, or —OX;
Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein R$^{15}$ and R$^{16}$ are independently selected from the group consisting of:
(a) C$_{1-6}$alkyl, unsubstituted or substituted with one or more of the substituents selected from:
(i) hydroxy,
(ii) oxo,
(iii) C$_{1-6}$alkoxy,
(iv) phenyl-C$_{1-3}$alkoxy,
(v) phenyl,
(vi) —CN,
(vii) halo,
(viii) —NR$^9$R$^{10}$, wherein R$^9$ and R$^{10}$ are as defined above,
(ix) —NR$^9$COR$^{10}$, wherein R$^9$ and R$^{10}$ are as defined above,
(x) —NR$^9$CO$_2$R$^{10}$, wherein R$^9$ and R$^{10}$ are as defined above,
(xi) —CONR$^9$R$^{10}$, wherein R$^9$ and R$^{10}$ are as defined above,
(xii) —COR$^9$, wherein R$^9$ is as defined above, and
(xiii) —CO$_2$R$^9$, wherein R$^9$ is as defined above;
(b) phenyl, unsubstituted or substituted with one or more to of the substituent(s) selected from:
(i) hydroxy,
(ii) C$_{1-6}$alkoxy,
(iii) C$_{1-6}$alkyl, (iv) $C_{2-5}$alkenyl,
(v) halo,
(vi) —CN,
(vii) —NO$_2$,
(viii) —CF$_3$,
(ix) —(CH$_2$)$_m$—NR$^9$R$^{10}$, wherein m, R$^9$ and R$^{10}$ are as defined above,
(x) —NR$^9$COR$^{10}$, wherein R$^9$ and R$^{10}$ are as defined above,
(xi) —NR$^9$CO$_2$R$^{10}$, wherein R$^9$ and R$^{10}$ are as defined above,
(xii) —CONR$^9$R$^{10}$, wherein R$^9$ and R$^{10}$ are as defined above,
(xiii) —CO$_2$NR$^9$R$^{10}$, wherein R$^9$ and R$^{10}$ are as defined above,
(xiv) —COR$^9$, wherein R$^9$ is as defined above, and
(xv) —CO$_2$R$^9$, wherein R$^9$ is as defined above;
Z is selected from:
(1) hydrogen,
(2) $C_{1-4}$alkyl, and
(3) hydroxy, with the proviso that if Y is —O—, Z is other than hydroxy, or if Y is —CHR$^{15}$—, then Z and R$^{15}$ may be joined together to form a double bond.

Particularly preferred compounds of formula (I) are those wherein: R$^1$ is selected from the group consisting of:
(1) $C_{1-6}$alkyl, substituted with one or more of the substituents selected from:
 (a) heterocycle, wherein the heterocycle is selected from the group consisting of:
  (A) benzimidazolyl,
  (B) imidazolyl,
  (C) isoxazolyl,
  (D) isothiazolyl,
  (E) oxadiazolyl,
  (F) pyrazinyl,
  (G) pyrazolyl,
  (H) pyridyl,
  (I) pyrrolyl,
  (J) tetrazolyl,
  (K) thiadiazolyl,
  (L) triazolyl, and
  (M) piperidinyl,
 and wherein the heterocycle is unsubstituted or substituted with one or more substituent(s) selected from:
  (i) $C_{1-6}$alkyl, unsubstituted or substituted with halo, —CF$_3$, —OCH$_3$, or phenyl,
  (ii) $C_{1-6}$alkoxy,
  (iii) oxo,
  (iv) thioxo,
  (v) cyano,
  (vi) —SCH$_3$,
  (vii) phenyl,
  (viii) hydroxy,
  (ix) trifluoromethyl,
  (x) —(CH$_2$)$_m$—NR$^9$R$^{10}$, wherein m is 0, 1 or 2, and R$^9$ and R$^{10}$ are independently selected from:
   (I) hydrogen,
   (II) $C_{1-6}$alkyl,
   (III) hydroxy$C_{1-6}$alkyl, and
   (IV) phenyl,
  (xi) —NR$^9$COR$^{10}$, wherein R$^9$ and R$^{10}$ are as defined above, and
  (xii) —CONR$^9$R$^{10}$, wherein R$^9$ and R$^{10}$ are as defined above,
R$^2$ and R$^3$ are independently selected from the group consisting of:
(1) hydrogen;
(2) $C_{1-6}$alkyl
(3) $C_{2-6}$alkenyl, and
(5) phenyl;
X is —O—;
R$^4$ is

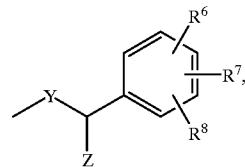

R$^5$ is phenyl, unsubstituted or substituted with halo;
R$^6$, R$^7$ and R$^8$ are independently selected from the group consisting of:
(1) hydrogen,
(2) $C_{1-6}$alkyl,
(3) halo, and
(4) —CF$_3$;
Y is —O—; and
Z is hydrogen or $C_{1-4}$alkyl;
and pharmaceutically acceptable salts thereof.

Particularly preferred compounds of formula (I) are:
4-(3-(1,2,4-triazolo)methyl)-2(S)-(3,5-bis(trifluoromethyl)benzyloxy)-3(S)-phenyl-morpholine;
4-(3-(1,2,4-triazolo)methyl)-2(S)-(3,5-bis(trifluoromethyl)benzyloxy)-3(R)-phenyl-morpholine;
4-(3-(5-oxo-1H,4H-1,2,4-triazolo)methyl)-2(S)-(3,5-bis(trifluoromethyl)benzyloxy)-3(S)-phenyl-morpholine; and
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; or a pharmaceutically acceptable salt thereof.

Further preferred NK-1 receptor antagonists are those described in International (PCT) Patent Specification No. WO 95/18124, i.e. compounds of formula (II):

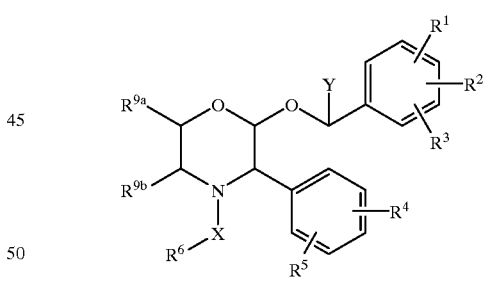

(II)

or a pharmaceutically acceptable salt or prodrug thereof, wherein
R$^1$ is hydrogen, halogen, $C_{1-6}$alkyl, $C_{1-6}$alkoxy, CF$_3$, NO$_2$, CN, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where R$^a$ and R$^b$ each independently represent hydrogen or $C_{1-4}$alkyl;
R$^2$ is hydrogen, halogen, $C_{1-6}$alkyl, $C_{1-6}$alkoxy substituted by $C_{1-4}$alkoxy or CF$_3$;
R$^3$ is hydrogen, halogen or CF$_3$;
R$^4$ is hydrogen, halogen, $C_{1-6}$alkyl, $C_{1-6}$alkoxy, CF$_3$, NO, CN, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where R$^a$ and R$^b$ each independently represent hydrogen or $C_{1-4}$alkyl;

$R^5$ is hydrogen, halogen, $C_{1-6}$alkyl, $C_{1-6}$alkoxy substituted by $C_{1-4}$alkoxy or $CF_3$;

$R^6$ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where Z is $C_{1-6}$alkylene or $C_{3-6}$cycloalkylene;

$R^7$ is hydrogen, $C_{1-4}$alkyl, $C_{3-7}$cycloalkyl or $C_{3-7}$cycloalkyl$C_{1-4}$alkyl, or $C_{2-4}$alkyl substituted by $C_{1-4}$alkoxy or hydroxyl;

$R^8$ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring of 4 to 7 ring atoms which may optionally contain an oxygen ring atom;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

X is an alkylene chain of 1 to 4 carbon atoms optionally substituted by oxo; and Y is a $C_{1-4}$alkyl group optionally substituted by a hydroxyl group;

with the proviso that if Y is $C_{1-4}$alkyl, $R^3$ is susbstituted at least by a group of formula $ZNR^7R^8$ as defined above.

Particularly preferred compounds of formula (II) are those of formula (IIa) and pharmaceutically acceptable salts thereof:

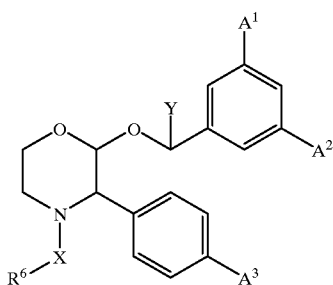

(IIa)

wherein:
$A^1$ is fluorine or $CF_3$;
$A^2$ is fluorine or $CF_3$;
$A^3$ is fluorine or hydrogen;
and X, Y and $R^6$ are as defined in relation to formula (II).

Particularly preferred compounds of formula (II) include:
2-(R)-(1-(R)-(3,5-bis(trifluoromethyl)phenyl)ethoxy)-4-(5-(dimethylamino) methyl-1,2,3-triazol-4-yl)methyl-3-(S)-phenylmorpholine;
2-(R)-(1-(R)-(3,5-bis(trifluoromethyl)phenyl)ethoxy)-4-(5-(dimethylamino) methyl-1,2,3-triazol-4-yl)methyl-3-(S)-(4-fluorophenyl)morpholine;

and pharmaceutically acceptable salts thereof.

Further preferred NK-1 receptor antagonists are those described in European Patent Specification No. WO 95/23798, i.e. compounds of formula (III):

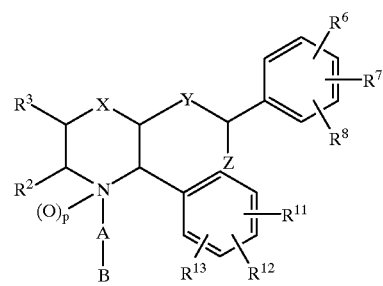

(III)

or a pharmaceutically acceptable salt thereof, wherein:
$R^2$ and $R^3$ are independently selected from the group consisting of:
(1) hydrogen,
(2) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —NR$^9$R$^{10}$, wherein $R^9$ and $R^{10}$ are independently selected from:
    (i) hydrogen,
    (ii) $C_{1-6}$alkyl,
    (iii) hydroxy-$C_{1-6}$alkyl, and
    (iv) phenyl,
  (i) —NR$^9$COR$^{10}$, wherein $R^9$ and $R^{10}$ are as defined above,
  (j) —NR$^9$CO$_2$R$^{10}$, wherein $R^9$ and $R^{10}$ are as defined above,
  (k) —CONR$^9$R$^{10}$, wherein $R^9$ and $R^{10}$ are as defined above,
  (l) —COR$^9$, wherein $R^9$ is as defined above, and
  (m) —CO$_2$R$^9$, wherein $R^9$ is as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —CONR$^9$R$^{10}$ wherein $R^9$ and $R^{10}$ are as defined above,
  (i) —COR$^9$ wherein $R^9$ is as defined above,
  (j) —CO$_2$R$^9$, wherein $R^9$ is as defined above;
(4) $C_{2-6}$alkynyl;
(5) phenyl, unsubstituted or substituted with one or more of the substituent(s) selected from:
  (a) hydroxy,
  (b) $C_{1-6}$alkoxy,
  (c) $C_{1-6}$alkyl,
  (d) $C_{2-5}$alkenyl,
  (e) halo, (f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above;

and the groups R$^2$ and R$^3$ may be joined together to form a carbocyclic ring selected from the group consisting of:
(a) cyclopentyl,
(b) cyclohexyl,
(c) phenyl, and wherein the carbocyclic ring is unsubstituted or substituted with one or more substituents selected from:
(i) C$_{1-6}$alkyl,
(ii) C$_{1-6}$alkoxy,
(iii) —NR$^9$R$^{10}$, wherein R$^9$ and R$^{10}$ are as defined above,
(iv) halo, and
(v) trifluoromethyl;

and the groups R$^2$ and R$^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl, and wherein the heterocyclic ring is unsubstituted or substituted with one or more substituent(s) selected from:
(i) C$_{1-6}$alkyl,
(ii) oxo,
(iii) C$_{1-6}$alkoxy,
(iv) —NR$^9$R$^{10}$, wherein R$^9$ and R$^{10}$ are as defined above,
(v) halo, and
(vi) trifluoromethyl;

R$^6$, R$^7$ and R$^8$ are independently selected from the group consisting of:
(1) hydrogen;
(2) C$_{1-6}$alkyl, unsubstituted or substituted with one or more of the substituents selected from:
(a) hydroxy,
(b) oxo,
(C) C$_{1-6}$alkoxy,
(d) phenyl-C$_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO2R$^9$, wherein R$^9$ is as defined above;
(4) C$_{2-6}$alkynyl;
(5) phenyl, unsubstituted or substituted with one or more of the substituent(s) selected from:
(a) hydroxy,
(b) C$_{1-6}$alkoxy,
(c) C$_{1-6}$alkyl,
(d) C$_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or C$_{1-5}$alkyl,
(11) —SOR$^{14}$, wherein R$^{14}$ is as defined above,
(12) —SO$_2$R$^{14}$, wherein R$^{14}$ is as defined above,
(13) NR$^9$COR$^{10}$, wherein R$^9$ and R$^{10}$ are as defined above,
(14) CONR$^9$COR$^{10}$, wherein R$^9$ and R$^{10}$ are as defined above,
(15) NR$^9$R$^{10}$, wherein R$^9$ and R$^{10}$ are as defined above,
(16) NR$^9$CO$_2$R$^{10}$, wherein R$^9$ and R$^{10}$ are as defined above,
(17) hydroxy,
(18) C$_{1-6}$alkoxy,
(19) COR$^9$, wherein R$^9$ is as defined above,
(20) CO$_2$R$^9$, wherein R$^9$ is as defined above,
(21) 2-pyridyl,
(22) 3-pyridyl,
(23) 4-pyridyl,
(24) 5-tetrazolyl,
(25) 2-oxazolyl, and

(26) 2-thiazolyl;

$R^{11}$, $R^{12}$ and $R^{13}$ are independently selected from the definitions of $R^6$, $R^7$ and $R^8$, or —OX;

A is selected from the group consisting of:
(1) $C_{1-6}$alkyl, unsubstituted or substituted with one or more of the substituents selected from:
   (a) hydroxy,
   (b) oxo,
   (c) $C_{1-6}$alkoxy,
   (d) phenyl-$C_{1-3}$alkoxy,
   (e) phenyl,
   (f) —CN,
   (g) halo, wherein halo is fluoro, chloro, bromo or iodo,
   (h) —$NR^9R^{10}$, wherein $R^9$ and $R^{10}$ are as defined above,
   (i) —$NR^9COR^{10}$, wherein $R^9$ and $R^{10}$ are as defined above,
   (j) —$NR^9CO_2R^{10}$, wherein $R^9$ and $R^{10}$ are as defined above,
   (k) —$CONR^9R^{10}$, wherein $R^9$ and $R^{10}$ are as defined above,
   (l) —$COR^9$, wherein $R^9$ is as defined above, and
   (m) —$CO_2R^9$, wherein $R^9$ is as defined above;
(2) $C_{2-6}$alkenyl, unsubstituted or substituted with one or more of the substituent(s) selected from:
   (a) hydroxy,
   (b) oxo,
   (c) $C_{1-6}$alkoxy,
   (d) phenyl-$C_{1-3}$alkoxy,
   (e) phenyl,
   (f) —CN,
   (g) halo,
   (h) —$CONR^9R^{10}$ wherein $R^9$ and $R^{10}$ are as defined above,
   (i) —$COR^9$ wherein $R^9$ is as defined above, and
   (j) —$CO_2R^9$, wherein $R^9$ is as defined above; and
(3) $C_{2-6}$alkynyl;

B is a heterocycle, wherein the heterocycle is selected from the group consisting of:

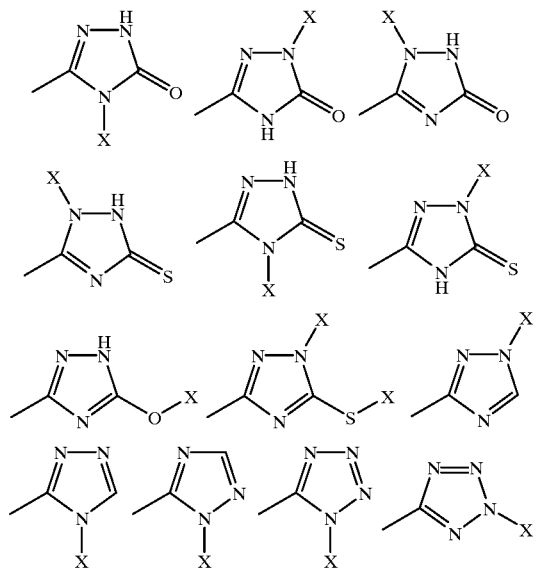

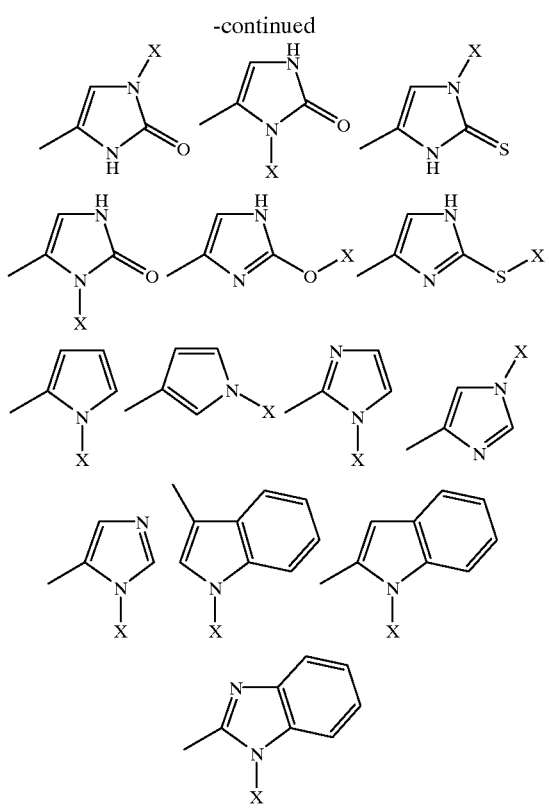

and wherein the heterocycle may be substituted in addition to —X with one or more substituent(s) selected from:
   (i) $C_{1-6}$alkyl, unsubstituted or substituted with halo, —$CF_3$, —$OCH_3$, or phenyl,
   (ii) $C_{1-6}$alkoxy,
   (iii) oxo,
   (iv) hydroxy,
   (v) thioxo,
   (vi) —$SR^9$, wherein $R^9$ is as defined above,
   (vii) halo,
   (viii) cyano,
   (ix) phenyl,
   (x) trifluoromethyl,
   (xi) —$(CH_2)_m$—$NR^9R^{10}$, wherein m is 0, 1 or 2, and $R^9$ and $R^{10}$ are as defined above,
   (xii) —$NR^9COR^{10}$, wherein $R^9$ and $R^{10}$ are as defined above,
   (xiii) —$CONR^9R^{10}$, wherein $R^9$ and $R^{10}$ are as defined above,
   (xiv) —$CO_2R^9$, wherein $R^9$ is as defined above, and
   (xv) —$(CH_2)_m$—$OR^9$, wherein m and $R^9$ are as defined above;

p is 0 or 1;

X is selected from:
   (a) —PO(OH)O— . $M^+$, wherein $M^+$ is a pharmaceutically acceptable monovalent counterion,
   (b) —PO(O—)$_2$ . 2$M^+$,
   (c) —PO(O—)$_2$ . $D^{2+}$, wherein $D^{2+}$ is a pharmaceutically acceptable divalent counterion,
   (d) —CH($R^4$)—PO(OH)O— . $M^+$, wherein $R^4$ is hydrogen or $C_{1-3}$alkyl,
   (e) —CH($R^4$)—PO(O—)$_2$ . 2$M^+$,
   (f) —CH($R^4$)—PO(O—)$_2$ . $D^{2+}$,
   (g) —$SO_3$— . $M^+$, (h) —CH(R$^4$)—SO$_3$— . M$^+$,
(i) —CO—CH$_2$CH$_2$—CO$_2$— . M$^+$,
(j) —CH(CH$_3$)—O—CO—R$^5$, wherein R$^5$ is selected from the group consisting of:

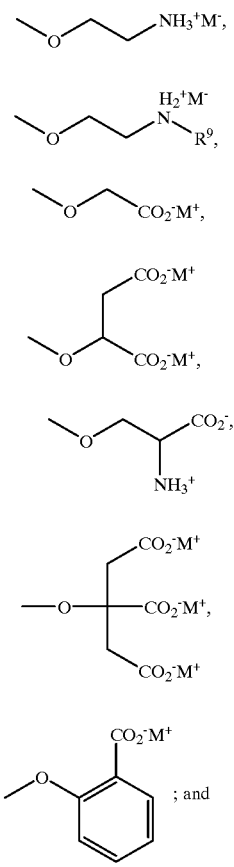

(k) hydrogen, with the proviso that if p is 0 and none of R$^{11}$, R$^{12}$ or R$^{13}$ are —OX, then X is other than hydrogen;

Y is selected from the group consisting of:
(1) a single bond,
(2) —O—,
(3) —S—,
(4) —CO—,
(5) —CH$_2$-,
(6) —CHR$^{15}$—, and
(7) —CR$^{15}$R$^{16}$—, wherein R$^{15}$ and R$^{16}$ are independently selected from the group consisting of:
(a) C$_{1-6}$alkyl, unsubstituted or substituted with one or more of the substituents selected from:
  (i) hydroxy,
  (ii) oxo,
  (iii) C$_{1-6}$alkoxy,
  (iv) phenyl-C$_{1-3}$alkoxy,
  (v) phenyl,
  (vi) —CN,
  (vii) halo,
  (viii) —NR$^9$R$^{10}$, wherein R$^9$ and R$^{10}$ are as defined above,
  (ix) —NR$^9$COR$^{10}$, wherein R$^9$ and R$^{10}$ are as defined above,
  (x) —NR$^9$CO$_2$R$^{10}$, wherein R$^9$ and R$^{10}$ are as defined above,
  (xi) —CONR$^9$R$^{10}$, wherein R$^9$ and R$^{10}$ are as defined above,
  (xii) —COR$^9$, wherein R$^9$ is as defined above, and
  (xiii) —CO$_2$R$^9$, wherein R$^9$ is as defined above;
(b) phenyl, unsubstituted or substituted with one or more of the substituent(s) selected from:
  (i) hydroxy,
  (ii) C$_{1-6}$alkoxy,
  (iii) C$_{1-6}$alkyl,
  (iv) C$_{2-5}$alkenyl,
  (v) halo,
  (vi) —CN,
  (vii) —NO$_2$,
  (viii) —CF$_3$,
  (ix) —(CH$_2$)$_m$—NR$^9$R$^{10}$, wherein m, R$^9$ and R$^{10}$ are as defined above,
  (x) —NR$^9$COR$^{10}$, wherein R$^9$ and R$^{10}$ are as defined above,
  (xi) —NR$^9$CO$_2$R$^{10}$, wherein R$^9$ and R$^{10}$ are as defined above,
  (xii) —CONR$^9$R$^{10}$, wherein R$^9$ and R$^{10}$ are as defined above,
  (xiii) —CO$_2$NR$^9$R$^{10}$, wherein R$^9$ and R$^{10}$ are as defined above,
  (xiv) —COR$^9$, wherein R$^9$ is as defined above, and
  (xv) CO$_2$R$^9$, wherein R$^9$ is as defined above;

Z is selected from:
(1) hydrogen,
(2) C$_{1-6}$alkyl, and
(3) hydroxy, with the proviso that if Y is —O—, Z is other than hydroxy, or if Y is —CHR$_{15}$—, then Z and R$^{15}$ may be joined together to form a double bond.

Particularly preferred compounds of formula (III) are those wherein:
R$^2$ and R$^3$ are independently selected from the group consisting of:
(1) hydrogen,
(2) C$_{1-6}$alkyl,
(3) C$_{2-6}$alkenyl, and
(4) phenyl;
R$^6$, R$^7$ and R$^8$ are independently selected from the group consisting of:
(1) hydrogen,
(2) C$_{1-6}$alkyl,
(3) fluoro,
(4) chloro,
(5) bromo,
(6) iodo, and
(7) —CF$_3$;
R$^{11}$, R$^{12}$ and R$^{13}$ are independently selected from the group consisting of:
(1) fluoro,
(2) chloro,
(3) bromo, and
(4) iodo;
A is unsubstituted $_{1-6}$alkyl;

B is selected from the group consisting of:

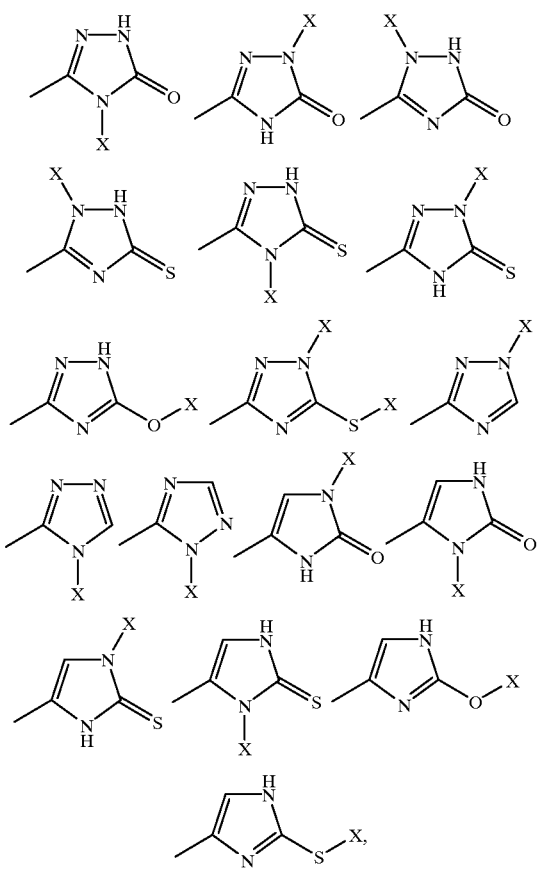

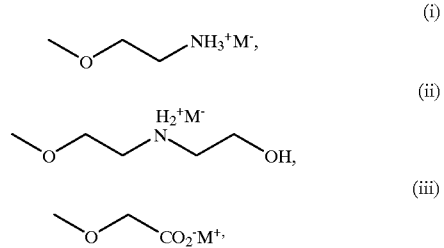

p is 0 or 1;
X is selected from:
(a) —PO(OH)O— . M$^+$, wherein M$^+$ is a pharmaceutically acceptable monovalent counterion,
(b) —PO(O—)$_2$ . 2M$^+$,
(c) —PO(O—)$_2$ . D$^{2+}$, wherein D$^{2+}$ is a pharmaceutically acceptable divalent counterion,
(d) —CH(R$^4$)—PO(OH)O— . M$^+$, wherein R$^4$ is hydrogen or C$_{1-3}$alkyl,
(e) —CH(R$^4$)—PO(O—)$_2$ . 2M$^+$,
(f) —CH(R$^4$)—PO(O—)$_2$ . D$^{2+}$,
(i) —CO—CH$_2$CH$_2$—CO$_2$— . M$^+$,
(j) —CH(CH$_3$)—O—CO—R$^5$, wherein R$^5$ is selected from the group consisting of:

(i)

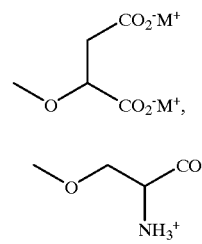

(ii)

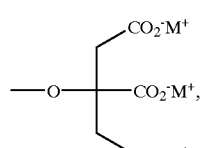

(iii)

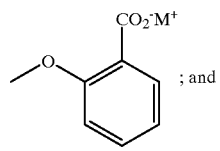

(iv)

(v)

(vi)

(vii)

; and

Y is —O—;
Z is hydrogen or C$_{1-6}$alkyl;

and pharmaceutically acceptable salts thereof.

Particularly preferred compounds of formula (III) include:

(1) 2-(S)-(3,5-bis(trifluoromethyl)benzyloxy)-3-(S)-phenyl-4-(3-(5-oxo-1H,4H-1,2,4-triazolo)methyl)morpholine N-oxide;
(2) 2-(S)-(3,5-bis(trifluoromethyl)benzyloxy)-3-(S)-phenyl-4-(3-(4-(ethoxycarbonyloxy-1-ethyl)-5-oxo-1H-1,2,4-triazolo)methyl)morpholine;
(3) 2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;
(4) 2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;
(5) 2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;
(6) 2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;
(7) 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

and pharmaceutically acceptable salts thereof.

Further preferred NK-1 receptor antagonists are those described in European Patent Specification No. WO 96/05181, i.e. compounds of formula (IV):

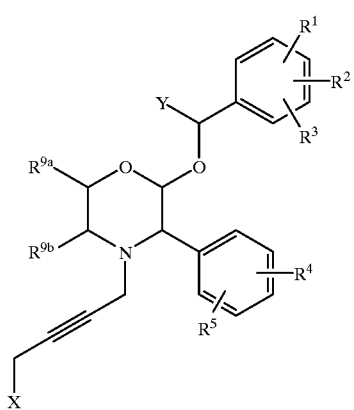

(IV)

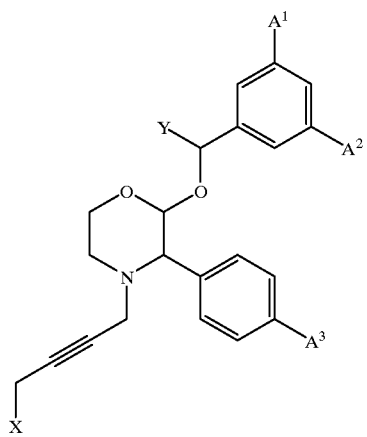

(IVa)

wherein
X is a group of the formula NR⁶R⁷ or a C- or N-linked imidazolyl ring;
Y is hydrogen or $C_{1-4}$alkyl optionally substituted by a hydroxy group;
$R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;
$R^2$ is hydrogen, halogen, $C_{1-6}$alkyl, $C_{1-6}$alkoxy substituted by $C_{1-4}$alkoxy or $CF_3$;
$R^3$ is hydrogen, halogen or $CF_3$;
$R^4$ is hydrogen, halogen, $C_{1-6}$alkyl, $C_{1-6}$alkoxy, hydroxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;
$R^5$ is hydrogen, halogen, $C_{1-6}$alkyl, $C_{1-6}$alkoxy substituted by $C_{1-4}$alkoxy or $CF_3$;
$R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;
$R^7$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;
or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, S(O) or $S(O)_2$ and which ring may be optionally substituted by one or two groups selected from hydroxy$C_{1-4}$alkyl, $C_{1-4}$alkoxy$C_{1-4}$alkyl, oxo, $COR^a$ or $CO_2R^a$ where $R^a$ is as previously defined;
or $R^6$ and $R^7$ together with the nitrogen atom to which they are attached, form a non-aromatic azabicyclic ring system of 6 to 12 ring atoms;
$R^8$ is hydrogen, $C_{1-4}$alkyl, hydroxy$C_{1-4}$alkyl or $C_{1-4}$alkoxy$C_{1-4}$alkyl; and
$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;
and pharmaceutically acceptable salts thereof.

Particularly preferred compounds of formula (IV) are those of formula (IVa) and pharmaceutically acceptable salts thereof:

wherein
$A^1$ is fluorine or $CF_3$;
$A^2$ is fluorine or $CF_3$;
$A^3$ is fluorine or hydrogen;
and X and Y are as defined in relation to formula (I).

Specific compounds of formula (IV) of use in the present invention include:

2-(R)-(1-(R)-(3,5-bis(trifluoromethyl)phenyl)ethoxy)-3-(S)-(4-fluorophenyl)-4-(4-morpholinobut-2-yn-yl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

4-(4-azetidinylbut-2-yn-yl)-2-(R)-(1-(R)-(3,5-bis(trifluoromethyl)phenyl) ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-imidazolylbut-2-yn-yl)morpholine; 2-(R)-(1-(R)-(3,5-bis(trifluoromethyl)phenyl)ethoxy)-3-(S)-(4-fluorophenyl)-4-(4-(N-methylpiperazinyl)but-2-yn-yl)morpholine;

4-(4-bis(2-methoxyethyl)aminobut-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-pyrrolidinobut-2-yn-yl)morpholine;

3-(S)-(4-fluorophenyl)-2-(R)-(1-(R)-(3-fluoro-5-(trifluoromethyl)phenyl) ethoxy)-4-(4-morpholinobut-2-yn-yl)morpholine;

3-(S)-(4-fluorophenyl)-4-(4-morpholinobut-2-yn-yl)-2-(R)-(1-(R)-(3-(trifluoromethyl)phenyl)ethoxy)morpholine;

4-(4-azetidinylbut-2-yn-yl)-3-(S)-(4-fluorophenyl)-2-(R)-(1-(R)-(3-(trifluoromethyl)phenyl)ethoxy)morpholine;

2-(R)-(1-(R)-(3,5-bis(trifluoromethyl)phenyl)ethoxy)-4-(4-(N-(2-methoxyethyl)-N-methyl)aminobut-2-yn-yl)-3-(S)-phenylmorpholine;

2-(R)-(1-(R)-(3,5-bis(trifluoromethyl)phenyl)ethoxy)-4-(4-(N-cyclopropyl-N-(2-methoxyethyl)amino)but-2-yn-yl)-3-(S)-phenylmorpholine;

2-(R)-(1-(R)-(3,5-bis(trifluoromethyl)phenyl)ethoxy)-4-(4-(N-isopropyl-N-(2-methoxyethyl)amino)but-2-yn-yl)-3-(S)-phenylmorpholine;

4-(4-(N,N-dimethylamino)but-2-yn-yl)-3-(S)-(4-fluorophenyl)-2-(R)-(1-(S)-(3-fluoro-5-(trifluoromethyl)phenyl-2-hydroxyethoxy)morpholine;

4-(4-azetidinylbut-2yn-yl)-3-(S)-(4-fluorophenyl)-2-(R)-(1-(S)-(3-fluoro-5-(trifluoromethyl)phenyl)-2-hydroxyethoxy)morpholine;

2-(R)-(1-(S)-(3,5-bis(trifluoromethyl)phenyl)-2-hydroxyethoxy)-4-(4-(N,N-dimethylamino)but-2-yn-yl)-3-(S)-(4-fluorophenyl)morpholine;

4-(4-azetidinylbut-2-yn-yl)-2-(R)-(1-(S)-(3,5-bis(trifluoromethyl)phenyl-2-hydroxyethoxy)-3-(S)-(4-fluorophenyl)morpholine;

4-(4-N-bis(2-methoxy)ethyl-N-methylamino)but-2-yn-yl)-2-(R)-(1-(R)-(3,5-bis(trifluoromethyl)phenyl)ethoxy)-3-(S)-(4-fluorophenyl)morpholine;

2-(R)-(1-(R)(3,5-bis(trifluoromethyl)phenyl)ethoxy)-3-(S)-(4-fluorophenyl)-4-(4-(2-(S)-(methoxymethyl)pyrrolidino)but-2-yn-yl)morpholine;

4-(4-(7-azabicyclo[2.2.1]heptano)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-4-(4-diisopropylaminobut-2-yn-yl)-3-(S)-(4-fluorophenyl) morpholine;

2-(R)-(1-(R)-(3-fluoro-5-(trifluoromethyl)phenyl)ethoxy)-4-(4-(2-(S)-(methoxymethyl)pyrrolidino)but-2-yn-yl)-3-(S)-phenylmorpholine;

2-(R)-(1-(R)-(3,5-bis(trifluoromethyl)phenyl)ethoxy)-3-(S)-(4-fluorophenyl)-4-(4-(2-(S)-(hydroxymethyl)pyrrolidino)but-2-yn-yl)morpholine;

and pharmaceutically acceptable salts thereof.

Another class of NK-1 receptor antagonists of use in the present invention is that described in European Patent Specification No. 0 436 334, i.e. compounds of formula (V):

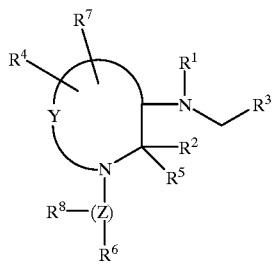

(V)

or a pharmaceutically acceptable salt thereof, wherein

Y is $(CH_2)_n$ wherein n is an integer from 1 to 4, and wherein any one of the carbon—carbon single bonds in said $(CH_2)_n$ may optionally be replaced by a carbon—carbon double bond, and wherein any one of the carbon atoms of said $(CH_2)_n$ may optionally be substituted with $R^4$, and wherein any one of the carbon atoms of said $(CH_2)_n$ may optionally be substituted-with $R^7$;

Z is $(CH_2)_m$ wherein m is an integer from 0 to 6, and wherein any one of the carbon—carbon single bonds of $(CH_2)_m$ may optionally be replaced by a carbon—carbon double bond or a carbon—carbon triple bond, and any one of the carbon atoms of said $(CH_2)_m$ may optionally be substituted with $R^8$;

$R^1$ is hydrogen or $C_{1-8}$alkyl optionally substituted with hydroxy, $C_{1-4}$alkoxy or fluoro;

$R^2$ is a radical selected from hydrogen, $C_{1-6}$ straight or branched alkyl, $C_{3-7}$cycloalkyl wherein one of the $CH_2$ groups in said cycloalkyl may optionally be replaced by NH, oxygen or sulphur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$C_{2-6}$alkyl, benzhydryl and benzyl, wherein each of said aryl and heteroaryl groups and the phenyl moieties of said benzyl, phenyl $C_{2-6}$alkyl and benzhydryl may optionally be substituted with one or more substituents independently selected from halo, nitro, $C_{1-6}$alkyl, $C_{1-6}$alkoxy, trifluoromethyl, amino, $C_{1-6}$alkylamino, $C_{1-6}$alkyl—O—CO, $C_{1-6}$alkyl—O—CO—$C_{1-6}$alkyl, $C_{1-6}$alkyl—CO—O, $C_{1-6}$alkyl—CO—$C_{1-6}$alkyl—O—, $C_{1-6}$alkyl—CO, $C_{1-6}$alkyl—CO—$C_{1-6}$alkyl-, di-$C_{1-6}$alkylamino, —CONH—$C_{1-6}$alkyl, $C_{1-6}$alkyl—CO—NH—$C_{1-6}$alkyl, —NHCOH and —NHCO—$C_{1-6}$alkyl; and wherein one of the phenyl moieties of said benzhydryl may optionally be replaced by naphthyl, thienyl, furyl or pyridyl;

$R^5$ is hydrogen, phenyl or $C_{1-6}$alkyl;

or $R^2$ and $R^5$ together with the carbon to which they are attached, form a saturated ring having from 3 to 7 carbon atoms wherein one of the $CH_2$ groups in said ring may optionally be replaced by oxygen, NH or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of the $(CH_2)$ groups in said cycloalkyl may optionally be replaced by NH, oxygen or sulphur;

wherein each of said aryl and heteroaryl groups may optionally be substituted with one or more substituents, and said $C_{3-7}$cycloalkyl may optionally be substituted with one or two substituents, each of said substituents being independently selected from halo, nitro, $C_{1-6}$alkyl, $C_{1-6}$alkoxy, trifluoromethyl, amino, $C_{1-6}$alkylamino, —CO—NH—$C_{1-6}$alkyl, $C_{1-6}$alkyl—CO—NH—$C_{16}$alkyl, —NHCOH and —NHCO—$C_{1-6}$alkyl;

$R^4$ and $R^7$ are each independently selected from hydroxy, halogen, halo, amino, oxo, cyano, methylene, hydroxymethyl, halomethyl, $C_{1-6}$alkylamino, di-$C_{1-6}$alkylamino, $C_{1-6}$alkoxy, $C_{1-6}$alkyl—O—CO, $C_{1-6}$alkyl—O—CO—$C_{1-6}$alkyl, $C_{1-6}$alkyl—CO—O, $C_{1-6}$alkyl—CO—$C_{1-6}$alkyl—O—, $C_{1-6}$alkyl—CO—, $C_{1-6}$alkyl—CO—$C_{1-6}$alkyl, and the radicals set forth in the definition of $R^2$;

$R^6$ is —NHCOR$^9$, —NHCH$_2$R$^9$, SO$_2$R$^8$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $C_{1-6}$alkyl, hydrogen, phenyl or phenyl$C_{1-6}$alkyl; with the proviso that (a) when m is 0, $R^8$ is absent, (b) when $R^4$, $R^6$, $R^7$ or $R^8$ is as defined in $R^2$, it cannot form together with the carbon to which it is attached, a ring with $R^5$, and (c) when $R^4$ and $R^7$ are attached to the same carbon atom, then either each of $R^4$ and $R^7$ is independently selected from hydrogen, fluoro and $C_{1-6}$alkyl, or $R^4$ and $R^7$, together with the carbon to which they are attached, for a $C_{3-6}$ saturated carbocyclic ring that forms a spiro compound with the nitrogen-containing ring to which they are attached.

A particularly preferred compound of formula (V) is (2S,3S)-cis-3-(2-methoxybenzylamino)-2-phenylpiperidine; or a pharmaceutically acceptable salt thereof.

Another class of NK-1 receptor antagonists of use in the present invention is that described in International Patent Specification No. WO 93/21155, i.e. compounds of formula (VI):

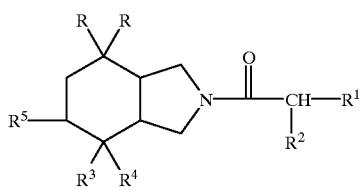
(VI)

or a pharmaceutically acceptable salt thereof, wherein radicals R are phenyl radicals optionally 2- or 3-substituted by a halogen atom or a methyl radical;

$R^1$ is optionally substituted phenyl, cyclohexadienyl, naphthyl, indenyl or optionally substituted heterocycle;

$R^2$ is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino;

$R^3$ is optionally 2-substituted phenyl;

$R^4$ is OH or fluorine when $R^5$ is H;

or $R^4$ and $R^5$ are OH;

or $R^4$ and $R^5$ together form a bond.

A particularly preferred compound of formula (VI) is (3aS, 4S, 7aS)-7,7-diphenyl-4-(2-methoxyphenyl)-2-[(2S)-(2-methoxyphenyl)propionyl] perhydroisoindol-4-ol; or a pharmaceutically acceptable salt thereof.

Another class of NK-1 receptor -antagonists of use in the present invention is that described in European Patent Specification No. 0 591 040, i.e. compounds of formula (VII):

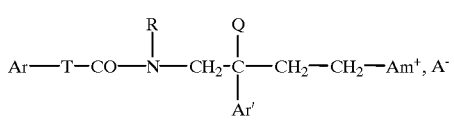
(VII)

wherein

Ar represents an optionally substituted mono-, di- or tricyclic aromatic or heteroaromatic group;

T represents a bond, a hydroxymethylene group, a $C_{1-4}$alkoxymethylene group or a $C_{1-5}$alkylene group;

Ar' represents a phenyl group which is unsubstituted or substituted by one or more substituents selected from halogen, preferably chlorine or fluorine, trifluoromethyl, $C_{1-4}$alkoxy, $C_{1-4}$alkyl where the said substituents may be the same or different; a thienyl group; a benzothienyl group; a naphthyl group; or an indolyl group;

R represents hydrogen, $C_{1-4}$alkyl, $\omega$-$C_{1-4}$alkoxy$C_{1-4}$alkyl, or $\omega$-$C_{2-4}$alkanoyloxy$C_{2-4}$alkyl;

Q represents hydrogen;

or Q and R together form a 1,2-ethylene, 1,3-propylene or 1,4-butylene group;

$Am^+$ represents the radical

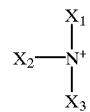

in which $X^1$, $X_2$ and $X_3$, together with the nitrogen atom to which they are attached, form an azabicyclic or azatricyclic ring system optionally substituted by a phenyl or benzyl group; and A represents a pharmaceutically acceptable anion.

A particularly preferred compound of formula (VII) is (+) 1-[2-[3-(3,4-dichlorophenyl)-1-[(3-isopropoxyphenyl) acetyl]-3-piperldinyl]ethyl]-4-phenyl-1-azabicyclo[2,2,2] octane; or a pharmaceutically acceptable salt, especially the chloride, thereof.

Another class of NK-1 receptor antagonists of use in the present invention is that described in European Patent Specification No. 0 532 456, i.e. compounds of formula (VIII):

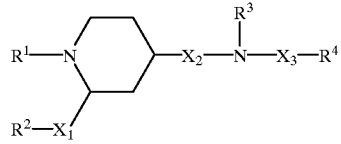
(VIII)

or a pharmaceutically acceptable salt thereof, wherein $R^1$ represents an optionally substituted aralkyl, aryloxyalykl, heteroaralkyl, aroyl, heteroaroyl, cycloalkylcarbonyl, aralkanoyl, heteroarylalkanoyl, aralkoxycarbonyl or arylcarbamoyl group or the acyl group of an α-amino acid optionally N-substituted by a lower alkanoyl or carbamoyl-lower alkanoyl group;

$R^2$ represents cycloalkyl or an optionally substituted aryl or heteroaryl group;

$R^3$ represents hydrogen, alkyl, carbamoyl or an alkanoyl or alkenoyl group optionally substituted by carboxy or esterified or amidated carboxy;

$R^4$ represents an optionally substituted aryl group or an optionally partially saturated heteroaryl group;

$X_1$ represents methylene, ethylene, a bond, an optionally ketalised carbonyl group or an optionally etherified hydroxymethylene group;

$X_2$ represents alkylene, carbonyl or a bond; and $X_3$ represents carbonyl, oxo-lower alkyl, oxo(aza)-tower alkyl, or an alkyl group optionally substituted by phenyl, hydroxymethyl, optionally esterified or amidated carboxy, or (in other than the α-position) hydroxy.

A particularly preferred compound of formula (VIII) is (2R*, 4S*)-2-benzyl-1-(3,5-dimethylbenzoyl)-N-(4-quinohnylmethyl)-4-piperidineamine; or a pharmaceutically acceptable salt thereof.

Another class of NK-1 receptor antagonists of use in the present invention is that described in European Patent Specification No. 0 443 132, i.e. compounds of formula (IX)

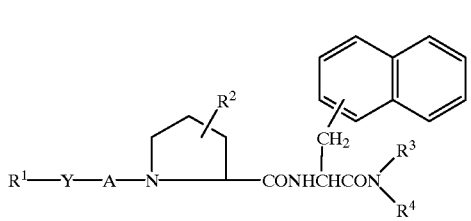
(IX)

or a pharmaceutically acceptable salt thereof, wherein $R^1$ is aryl, or a group of the formula:

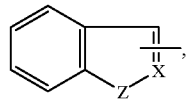

X is CH or N; and

Z is O or N—R⁵, in which R⁵ is hydrogen or lower alkyl;
R² is hydroxy or lower alkoxy;
R³ is hydrogen or optionally substituted lower alkyl;
R⁴ is optionally substituted ar(lower)alkyl;
A is carbonyl or sulfonyl; and
Y is a bond or lower alkenylene.

A particularly preferred compound of formula (IX) is the compound of formula (IXa)

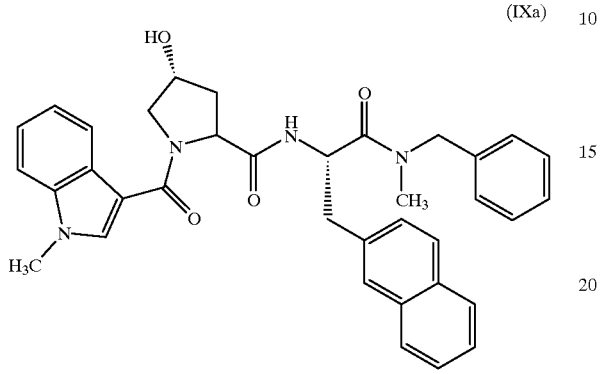

(IXa)

or a pharmaceutically acceptable salt thereof.

Another class of NK-1 receptor antagonists of use in the present invention is that described in International Patent Specification No. WO 92/17449, i.e. compounds of the formula (X)

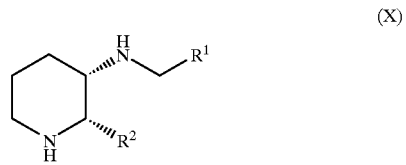

(X)

or a pharmaceutically acceptable salt thereof, wherein
R¹ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $C_{3-7}$cycloalkyl may optionally be substituted with one or two substituents, said substituents being independently selected from chloro, fluoro, bromo, iodo, nitro, $C_{1-10}$alkyl optionally substituted with from one to three fluoro groups, $C_{1-10}$alkoxy optionally substituted with from one to three fluoro groups, amino, $C_{1-10}$alkyl—S—, $C_{1-10}$alkyl—S(O)—, $C_{1-10}$alkyl—SO₂—, phenyl, phenoxy, $C_{1-10}$alkyl—SO₂NH—, $C_{1-10}$alkyl—SO₂NH—$C_{1-10}$alkyl-, $C_{1-10}$alkylamino-di$C_{1-10}$alkyl-, cyano, hydroxy, cycloalkoxy having 3 to 7 carbon atoms, $C_{1-6}$alkylamino, $C_{1-6}$dialkylamino, HC(O)NH— and $C_{1-10}$alkyl-C(O)NH—; and
R² is thienyl, benzhydryl, naphthyl or phenyl optionally substituted with from one to three substituents independently selected from chloro, bromo, fluoro, iodo, cycloalkoxy having 3 to 7 carbon atoms, $C_{1-10}$alkyl optionally substituted with from one to three fluoro groups and $C_{1-10}$alkoxy optionally substituted with from one to three fluoro groups.

A particularly preferred compound of formula (X) is (2S,3S)-3-(2-methoxy-5-trifluoromethoxybenzyl)-amino-2-phenylpiperidine; or a pharmaceutically acceptable salt thereof.

Another class of NK-1 receptor antagonists of use in the present invention is that described in International Patent Specification No. WO 95/08549, i.e. compounds of formula (XI)

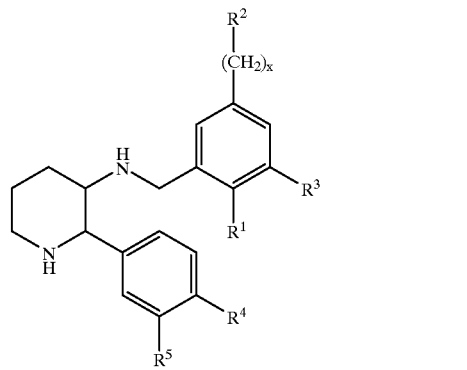

(XI)

or a pharmaceutically acceptable salt thereof, wherein
R¹ is a $C_{1-4}$alkoxy group;
R² is

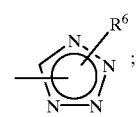

;

R³ is a hydrogen or halogen atom;
R⁴ and R⁵ may each independently represent a hydrogen or halogen atom, or a $C_{1-4}$alkyl, $C_{1-4}$alkoxy or trifluoromethyl group;
R⁶ is a hydrogen atom, a $C_{1-4}$alkyl, $(CH_2)_m$cyclopropyl, —S(O)ₙ$C_{1-4}$alkyl, phenyl, NR⁷R⁸, CH₂C(O)CF₃ or trifluoromethyl group;
R⁷ and R⁸ may each independently represent a hydrogen atom, or a $C_{1-4}$alkyl or acyl group;
x represents zero or 1;
n represents zero, 1 or 2; and
m represents zero or 1.

Particularly preferred compounds of formula (XI) are (2-methoxy-5-tetrazol-1-yl-benzyl)-([2S,3S]-2-phenyl-piperidin-3-yl)-amine; and [2-methoxy-5-(5-trifluoromethyl-tetrazol-1-yl)-benzyl]-([2S,3S]-2-phenyl-piperidin-3-yl)-amine; or a pharmaceutically acceptable salt thereof.

Another class of tachykinin antagonists of use in the present invention is that described in International Patent Specification No. WO 95/14017, i.e. compounds of formula (XII)

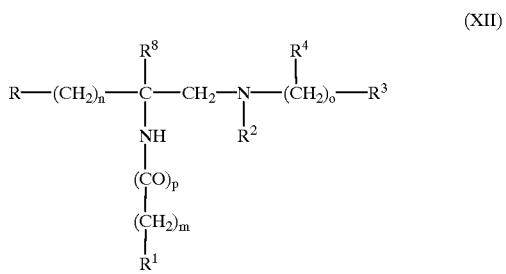

(XII)

or a pharmaceutically acceptable salt thereof, wherein m is zero, 1, 2 or 3;
n is zero or 1;
o is zero, 1 or 2;
p is zero or 1;
R is phenyl, 2- or 3-indolyl, 2- or 3-indolinyl, benzothienyl, benzofuranyl, or naphthyl;
which R groups may be substituted with one or two halo, $C_{1-3}$alkoxy, trifluoromethyl, $C_{1-4}$alkyl, phenyl-$C_{1-3}$alkoxy, or $C_{1-4}$alkanoyl groups;
$R^1$ is trityl, phenyl, diphenylmethyl, phenoxy, phenylthio, piperazinyl, piperidinyl, pyrrolidinyl, morpholinyl, indolinyl, indolyl, benzothienyl, hexamethyleneiminyl, benzofuranyl, tetrahydropyridinyl, quinolinyl, isoquinolinyl, reduced quinolinyl, reduced isoquinolinyl, phenyl-($C_{1-4}$alkyl)-, phenyl-($C_{1-4}$alkoxy)-, quinolinyl-($C_{1-4}$alkyl)-, isoquinolinyl-($C_{1-4}$alkyl)-, reduced quniolinyl-($C_{1-4}$alkyl)-, reduced isoquinolinyl-($C_{1-4}$alkyl)-, benzoyl-($C_{1-3}$alkyl)-, $C_{1-4}$alkyl, or —NH—$CH_2$—$R^5$;
any one of which $R^1$ groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;
or any one of which $R^1$ groups may be substituted with phenyl, piperazinyl, $C_{3-8}$cycloalkyl, benzyl, $C_{1-4}$alkyl, piperidinyl, pyridinyl, pyrimidinyl, $C_{2-6}$alkanoylamino, pyrrolidinyl, $C_{2-6}$alkanoyl, or $C_{1-4}$alkoxycarbonyl;
any one of which groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;
or $R^1$ is amino, a leaving group, hydrogen, $C_{1-4}$alkylamino, or di($C_{1-4}$alkyl)amino;
$R^5$ is pyridyl, anilino-($C_{1-3}$alkyl)-, or aminocarbonyl;
$R^2$ is hydrogen, $C_{1-4}$alkyl, $C_{1-4}$alkylsulfonyl, carboxy-($C_{1-3}$alkyl)-, $C_{1-3}$alkoxycarbonyl-($C_{1-3}$alkyl)-, or —CO—$R^6$;
$R^6$ is hydrogen, $C_{1-4}$alkyl, $C_{1-3}$haloalkyl, phenyl, $C_{1-3}$alkoxy, $C_{1-3}$hydroxyalkyl, amino, $C_{1-4}$alkylamino, di($C_{1-4}$alkyl)amino, or —$(CH_2)_q$—$R^7$;
q is zero to 3;
$R^7$ is carboxy, $C_{1-4}$alkoxycarbonyl, $C_{1-4}$alkylcarbonyloxy, amino, $C_{1-4}$alkylamino, di($C_{1-4}$alkyl)amino, $C_{1-6}$alkoxycarbonylamino, or phenoxy, phenylthio, piperazinyl, piperidinyl, pyrrolidinyl, morpholinyl, indolinyl, indolyl, benzothienyl, benzofuranyl, quinolinyl, phenyl-($C_{1-4}$alkyl)-, quinolinyl-($C_{1-4}$alkyl)-, isoquinolinyl-($C_{1-4}$alkyl)-, reduced quinolinyl-($C_{1-4}$alkyl)-, reduced isoquinolinyl-($C_{1-4}$alkyl)-, benzoyl-$C_{1-3}$alkyl;
any one of which aryl or heterocyclic $R^7$ groups may be substituted with halo, trifluoromethyl, $C_{1-4}$alkoxy, $C_{1-4}$alkyl, amino, $C_{1-4}$alkylamino, di($C_{1-4}$alkyl)amino, or $C_{2-4}$alkanoylamino;
or any one of which $R^7$ groups may be substituted with phenyl, piperazinyl, $C_{3-8}$cycloalkyl, benzyl, piperidinyl, pyridinyl, pyrimidinyl, pyrrolidinyl, $C_{2-6}$alkanoyl, or $C_{1-4}$alkoxycarbonyl;
any of which groups may be substituted with halo, trifluoromethyl, amino, $C_{1-4}$alkoxy, $C_{1-4}$alkyl, $C_{1-4}$alkylamino, di($C_{1-4}$alkyl)amino, or $C_{2-4}$alkanoylamino;
$R^8$ is hydrogen or $C_{1-6}$alkyl;
$R^3$ is phenyl, phenyl-($C_{1-6}$alkyl)-, $C_{1-3}$cycloalkyl, $C_{5-8}$cycloalkenyl, $C_{1-8}$alkyl, naphthyl, $C_{2-8}$alkenyl, or hydrogen;
any one or which groups except hydrogen may be substituted with one or two halo, $C_{1-3}$alkoxy, $C_{1-3}$alkylthio, nitro, trifluoromethyl, or $C_{1-3}$alkyl groups; and
$R^4$ is hydrogen or $C_{1-3}$alkyl;
with the proviso that if RI is hydrogen or halo, $R^3$ is phenyl, phenyl-($C_{1-6}$alkyl)-, $C_{3-8}$cycloalkyl, $C_{5-8}$cycloalkenyl, or naphthyl.

A particularly preferred compound of formula (XII) is [N-(2-methoxybenzyl)acetylamino]-3-(1H-indol-3-yl)-2-[N-(2-(4-piperidin-1-yl)piperidin-1-yl)acetylamino] propane; or a pharmaceutically acceptable salt thereof.

The above compounds are only illustrative of NK-1 receptor antagonists which are currently under investigation. As this listing of compounds is not meant to be comprehensive, the use and methods of the present invention may employ any NK-1 receptor antagonist, in particular a NK-1 receptor antagonist which is orally active, long acting and CNS-penetrant. Accordingly the present invention is not strictly limited to any particular structural class of compound.

The preferred compounds of formulae (I), (II), (III) and (IV) will have the 2- and 3-substituents on the morpholine ring in the cis arrangement, the preferred stereochemistry being as shown in the following general formula:

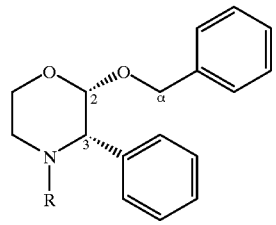

Where the benzyloxy moiety is α-substituted, the preferred stereochemistry of the a-carbon is either (R) when the substituent is an alkyl (e.g. methyl) group or (S) when the substituent is a hydroxyalkyl (e.g. hydroxymethyl) group.

Unless otherwise defined herein, suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, sec-butyl and tert-butyl.

Unless otherwise defined herein, suitable alkenyl groups include straight-chained and branched alkenyl groups containing from 2 to 6 carbon atoms. Typical examples include vinyl and allyl groups.

Unless otherwise defined herein, suitable alkynyl groups include straight-chained and branched alkynyl groups containing from 2 to 6 carbon atoms. Typical examples include ethynyl and propargyl groups.

Unless otherwise defined herein, suitable cycloalkyl groups include groups containing from 3 to 7 carbon atoms. Particular cycloalkyl groups are cyclopropyl and cyclohexyl.

Unless otherwise defined herein, suitable aryl groups include phenyl and naphthyl groups.

A particular aryl-$C_{1-6}$alkyl, e.g. phenyl-$C_{1-6}$alkyl, group is benzyl.

Unless otherwise defined herein, suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups.

The term "halogen" as used herein includes fluorine, chlorine, bromine and iodine.

The compounds of use in this invention may have one or more asymmetric centres and can therefore exist as enantiomers and possibly as diastereoisomers. It is to be understood that the present invention relates to the use of all such isomers and mixtures thereof.

Suitable pharmaceutically acceptable salts of the NK-1 receptor antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Suitable pharmaceutically acceptable salts of the antipsychotic agents used in combination with a NK-1 receptor antagonist according to the present invention include those salts described above in relation to the salts of NK-1 receptor antagonists.

The present invention accordingly provides the use of a NK-1 receptor antagonist selected from the compounds of formulae (I), (II), (III), (IV), (V), (VI), (VII), (VIII), (IX), (X), (XI) and (XII) for the manufacture of a medicament for the treatment or prevention of mania.

The present invention also provides a method for the treatment or prevention of mania, which method comprises administration to a patient in need of such treatment of an effective amount of a NK-1 receptor antagonist selected from the compounds of formulae (I), (II), (III), (IV), (V), (VI), (VII), (VII), (IX), (X), (XI) and (XII).

In a further aspect of the present invention, there is provided a pharmaceutical composition for the treatment or prevention of mania comprising a NK-1 receptor antagonist selected from the compounds of formulae (I), (II), (III), (IV), (V), (VI), (VII), (VIII), (IX), (X), (XI) and (XII), together with at least one pharmaceutically acceptable carrier or excipient.

Preferably the compositions according to the present invention are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof.

When referring to these preformulation compositions as homogeneous, it is meant that the active ingredient is dispersed evenly throughout the composition so that the composition may be readily subdivided into equally effective unit dosage forms such as tablets, pills and capsules.

This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Preferred compositions for administration by injection include those comprising a NK-1 receptor antagonist as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Lposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithn) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above.

Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

Compositions in the form of tablets, pills, capsules or wafers for oral administration are particularly preferred.

The present invention further provides a process for the preparation of a pharmaceutical composition comprising a NK-1 receptor antagonist and an antipsychotic agent, which process comprises bringing a NK-1 receptor antagonist and an antipsychotic agent, into association with a pharmaceutically acceptable carrier or excipient.

When administered in combination, either as a single or as separate pharmaceutical composition(s), the NK-1 receptor antagonist and an antipsychotic agent are presented in a ratio which is consistent with the manifestation of the desired effect. In particular, the ratio by weight of the NK-1 receptor antagonist and the antipsychotic agent will suitably be between 0.001 to 1 and 1000 to 1, and especially between 0.01 to 1 and 100 to 1.

A minimum dosage level for the NK-1 receptor antagonist is about 5 mg per day, preferably about 10 mg per day and especially about 20 mg per day. A maximum dosage level for the NK-1 receptor antagonist is about 1500 mg per day, preferably about 1000 mg per day and especially about 500 mg per day. The compounds are administered one to three times daily, preferably once a day.

A minimum dosage level for the antipsychotic agent will vary depending upon the choice of agent, but is typically about 0.5 mg per day for the most potent compounds or about 20 mg per day for less potent compounds. A maximum dosage level for the antipsychotic agent is typically 30 mg per day for the most potent compounds or 200 mg per day for less potent compounds. The compounds are administered one to three times daily, preferably once a day.

It will be appreciated that the amount of the NK-1 receptor antagonist required for use in the treatment or prevention of mania will vary not only with the particular compounds or compositions selected but also with the route of administration, the nature of the condition being treated, and the age and condition of the patient, and will ultimately be at the discretion of the patient's physician or pharmacist.

When used in combination, it will be appreciated that the amount of the NK-1 receptor antagonist and the antipsychotic agent required for use in the treatment or prevention of mania will vary not only with the particular compounds or compositions selected but also with the route of administration, the nature of the condition being treated, and the age and condition of the patient, and will ultimately be at the discretion of the patient's physician or pharmacist.

The compounds of formulae (I), (II), (III), (IV), (V), (VI), (VII), (VIII), (IX), (X), (XI) and (XII) may be prepared by the methods described in EP-A-0 577 394 (or WO 95/16679), WO 95/18124, WO 95/23798, WO 96/05181, EP-A-0 436 334, WO 93/21155, EP-A-0 591 040, EP-A-0 532 456, EP-A-0 443 132, WO 92/17449, WO 95/08549 and WO 95/14017, respectively.

Particularly preferred NK-1 receptor antagonists of the formulae (I), (II), (III), (IV), (V), (VI), (VII), (VIII), (IX), (X), (XI) and (XII) for use in the present invention are compounds which are potent NK-1 receptor antagonists, i.e. compounds with an NK-1 receptor affinity ($IC_{50}$) of less than 10 nM.

A particularly preferred class of NK-1 receptor antagonist of use in the present invention are those compounds which are orally active, long acting and CNS-penetrant. Such compounds may be identified using the pharmacological assays described hereinafter. The use of this sub-class of NK-1 antagonists in the treatment or prevention of mania represents a further aspect of the present invention.

Thus, the present invention provides the use of a CNS penetrant NK-1 receptor antagonist in an oral, once-a-day medicament for the treatment of mania. The compounds of this class advantageously exhibit a rapid onset of action and a reduced side-effect profile when compared against conventional treatments of mania.

In particular, the present invention provides a means for the identification of NK-1 receptor antagonists which would be especially effective in an oral once-a-day medicament for the treatment of mania.

The exceptional pharmacology of the class of orally active, long acting, CNS-penetrant NK-1 receptor antagonists (as hereinafter defined) of use in the present invention enables the treatment of mania, without the need for concomitant therapy and in particular; without the need for concomitant use of antipsychotic agents.

Furthermore, the exceptional pharmacology of the class of NK-1 receptor antagonists of use in the present invention results in a rapid onset of action.

The present invention accordingly provides the use of an orally active, long acting, CNS-penetrant NK-1 receptor antagonist (as hereinafter defined) for the manufacture of a medicament adapted for oral administration for the treatment or prevention of mania.

The present invention also provides a method for the treatment or prevention of mania, which method comprises the oral administration to a patient in need of such treatment of an effective amount of an orally active, long acting, CNS-penetrant NK-1 receptor antagonist (as hereinafter defined).

In a further aspect of the present invention, there is provided an oral pharmaceutical composition for the treatment of mania which comprises an orally active, long acting, CNS-penetrant NK-1 receptor antagonist (as hereinafter defined), together with a pharmaceutically acceptable carrier or excipient.

There exists a patient population in whom mania is inadequately treated with lithium. Furthermore, some patients may be adversely affected by the side-effects of lithium.

The present invention accordingly provides the use of an orally active, long acting, CNS-penetrant NK-1 receptor antagonist for the manufacture of a medicament adapted for oral administration for the treatment or prevention of mania in a patient who is non-responsive to lithium or for whom lithium is contraindicated.

The present invention also provides a method for the treatment or prevention of mania in a patient who is non-responsive to lithium or for whom lithium is contraindicated, which method comprises oral administration to a patient in need of such treatment of an effective amount of an orally active, long acting, CNS-penetrant NK-1 receptor antagonist.

There also exists a patient population in whom mania is inadequately treated with antipsychotic agents. Furthermore, some patients may be adversely affected by the side-effects of antipsychotic agents such that the use of an antipsychotic agent, alone or in combination with a NK-1 receptor antagonist, would be undesirable.

The present invention accordingly provides the use of an orally active, long acting, CNS-penetrant NK-1 receptor antagonist for the manufacture of a medicament adapted for oral administration for the treatment or prevention of mania in a patient who is non-responsive to antipsychotic agents or for whom antipsychotic agents are is contraindicated.

The present invention also provides a method for the treatment or prevention of mania in a patient who is non-responsive to antipsychotic agents or for whom antipsychotic agents are is contraindicated, which method comprises oral administration to a patient in need of such treatment of an effective amount of an orally active, long acting, CNS-penetrant NK-1 receptor antagonist.

Preferred NK-1 receptor antagonists for use in the present invention as orally active, long acting, CNS-penetrant NK-1 receptor antagonists are selected from the classes of compounds described in European Patent Specification No. 0 577 394, and International Patent Specification Nos. 95/08549, 95118124, 95/23798 and 96/05181, and International Patent Application No. PCT/GB97/01630. The preparation of such compounds is fully described in the aforementioned publications.

Thus, further particularly preferred NK-1 receptor antagonists of use in the present invention include:

2-(S)-(3,5-bis(trifluoromethyl)benzyloxy)-3(S)-(4-fluorophenyl)-4-(3-(5-oxo-1H,4H-1,2,4-triazolo)methyl) morpholine;

2-(R)-(1-(R)-(3,5-bis(trifluoromethyl)phenyl)ethoxy)-4-(3-(5-oxo-1H, 4H-1,2,4-triazolo)methyl)-3-(S)-phenyl-morpholine;

2-(S)-(3,5-bis(trifluoromethyl)benzyloxy)-4-(3-(5-oxo-1H, 4H-1,2,4-triazolo)methyl)-3-(S)-phenyl-morpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo) methyl)morpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl) morpholine;

(3S,5R,6S)-3-[2-cyclopropoxy-5-(trifluoromethoxy)phenyl-1-oxa-7-aza-spiro[4.5]decane;

(3R,5R,6S)-3-[2-cyclopropoxy-5-(trifluoromethoxy) phenyl-1-oxa-7-aza-spiro[4.5]decane;

or a pharmaceutically acceptable salt thereof.

Full descriptions of the preparation of the NK-1 receptor antagonists may be found in the references cited herein.

Two compounds of use as orally active, long acting, CNS penetrant NK-1 receptor antagonists in the present invention which are described in International Patent Application No. PCT/GB97/01630 may be prepared according to the following methods:

PREPARATION 1

(2S)-1-tert-Butoxycarbonyl-2-phenylpiperidin-3-one

Dimethyl sulfoxide (20.80 ml, 22.90 g, 29.3 mmol) in dichloromethane (75 ml) was added dropwise to a cooled (−70° C.) solution of oxalyl chloride (13.95 ml, 20.30 g, 160 mmol) in dichloromethane (350 ml). The mixture was stirred at −70° C. for 15 minutes, then (2S,3S)-1-tert-butoxycarbonyl-3-hydroxy-2-phenylpiperidine (prepared by the method described in European Patent Specification number 0 528 495-A; 36.91 g, 133 mmol) in dichloromethane (150 ml) was added dropwise. The mixture was stirred at −70° C. for 20 minutes, then allowed to warm to −30° C. The mixture was cooled to −50° C. and triethylamine (55.95 ml, 40.45 g, 400 mmol) was added slowly. The mixture was allowed to warm to 0° C. and diluted with ice-cooled dichloromethane (250 ml). The mixture was washed with ice cold aqueous citric acid solution (5%, 2×300 ml) and water (300 ml), dried (MgSO$_4$), and the solvent was evaporated under reduced pressure to give the title compound as a yellow oil (42.3 g), which was used immediately without further purification. $^1$H NMR (250 MHz, CDCl$_3$)δ 7.5–7.3 (5H, m), 5.8 (1H, br s), 4.2 (1H, br s), 3.4 (1H, m), 2.6 (2H, m), 2.0 (2H, m), and 1.54 (9H, s).

PREPARATION 2

(2S,3R)-1-tert-Butoxycarbonyl-3-hydroxy-3-(2-methylene-3-phenoxypropyl)-2-phenylpiperidine A solution of 3-(chloromagnesio)-2-(phenoxymethyl)-1-propene in THF (0.91M, 3 ml) (Louw et. al., Tetrahedron, 48, 6087–6104, 1992, prepared from 2.74 mmol of 3-chloro-2-(phenoxymethyl)-1-propene) was slowly added to a solution of (2S)-1-tert-butoxycarbonyl-2-phenylpiperidin-3-one (Preparation 1) in THF (3 ml). The mixture was stirred at room temperature for 1 hours, then saturated aqueous ammonium chloride (20 ml) was added and the mixture was extracted with ethyl acetate (20 ml). The organic phase was washed with brine, dried (MgSO$_4$) and the solvent was evaporated under reduced pressure. The residue was purified by column chromatography on silica gel, eluting with hexane/ethyl acetate (100:0 increasing to 80:20) to give the title compound. $^1$H NMR (360 MHz, CDCl$_3$)δ 7.48 (2H, d, J=6.9 Hz), 7.35–7.2 (6H, m), 6.9–6.88 (3H, m), 5.4 (1H, s), 5.15 (2H, d, J=13.7 Hz), 4.61 (2H, s), 4.11 (2H, m), 3.17 (1H, m), 2.66 and 2.59 (2H, AB d, J=14.0 Hz), 1.95 (2H, m), 1.79 (2H, m), and 1.36 (9H, s). m/z (ES$^+$) 424 (M+1).

PREPARATION 3

(5R,6S)-3-Methylene-6-phenyl-1-oxa-7-(tert-butoxycarbonyl)aza-spiro[4.5]decane

To a cooled(−80° C.) solution of (2S,3R)-1-tert-butoxycarbonyl-3-hydroxy-3-(2-methylene-3-phenoxypropyl)-2-phenylpiperidine (Preparation 2, 1.53 g, 3.62 mmol) in THF (20 ml) was added n-butyl lithium (2.5M in hexanes, 1.45 ml, 3.62 mmol) followed by a solution of zinc chloride (0.5M in THF, 7.24 ml, 3.62 mmol). The solution was allowed to warm to room temperature and tetrakis(triphenylphosphine)palladium (0) (0.23 g, 0.2 mmol) was added. The mixture was degassed with bubbling nitrogen and heated under reflux for 16 hours. The mixture was cooled and the solvent was evaporated under reduced pressure. The residue was partitioned between ethyl acetate and 2M sodium hydroxide. The organic phase was washed with saturated brine, dried (MgSO$_4$) and purified by chromatography on a column containing silica gel (eluting with hexane containing increasing proportions of ethyl acetate between 0% to 5%). Evaporation of the fractions gave (6S,5R)-3-methylene-6-phenyl-1-oxa-7-(tert-butoxycarbonyl)aza-spiro[4.5]decane. $^1$H NMR (360 MHz, CDCl$_3$)δ 7.58 (2H, d, J=8.4 Hz), 7.32–7.21 (3H, m), 5.23 (1H, s), 5.06 (1H. m), 4.97 (1H, m), 4.39 (2H, AB d, J=13.3 Hz), 3.99 (1H, dd, J=13.3, 4.48 Hz), 2.83 (1H, ABd J=15.5 Hz), 2.7 (1H, td J=12.5, 3.93 Hz), 2.5 (1H, ABd, J=15.4 Hz), 2.15 (2H, td, J=12., .4 Hz), 1.69 (2H, m), and 1.46 (9H, s). m/z (ES$^+$) 329 (M+2H-$^t$BuOCO).

PREPARATION 4

(5R,6S)-3-Keto-6-phenyl-1-oxa-7-(tert-butoxycarbonyl) aza-spiro[4.5]decane

Through a cooled (−80° C.) solution of (5R,6S)-3-methylene-6-phenyl-1-oxa-7-(tert-butoxycarbonyl)aza-spiro[4.5]decane (Preparation 3; 0.665 g) in dichloromethane (5 ml) and methanol (5 ml) was bubbled a mixture of ozone and oxygen for 45 minutes. After the solution had been purged with nitrogen, dimethyl sulphide (0.5 ml) was added and then stirred under nitrogen at room temperature for 16 hours. The solvent was removed in vacuo and the residue partitioned between ethyl acetate and water. The organic phase was dried ($MgSO_4$), evaporated and the residue purified by chromatography on a column containing silica gel (eluting with hexane containing increasing proportions of ethyl acetate between 0% to 10%). Evaporation of the fractions gave the title compound. $^1$H NMR (250 MHz, $CDCl_3$)δ 7.58 (2H, d, J=6.2 Hz), 7.37–7.26 (3H, m), 5.3 (1H, s), 4.15 and 4.09 (2H, AB d, J=17.4 Hz), 3.97 (1H, m), 2.80 (1H, td, J=12.9, 4.0 Hz), 2.74 and 2.48 (2H, ABd, J=18.1 Hz), 2.29 (2H, m), 1.88–1.63 (2H, m), and 1.44 (9H, s). m/z ($ES^+$) 332 (M+1).

PREPARATION 5
(5R,6S)-3-Trifluoromethylsulfonyloxy-6-phenyl-1-oxa-7-(tert-butoxycarbonyl)aza-spiro[4.5]dec-3-ene To a cooled (−80° C.) solution of 1M sodium hexamethyldisilazide (0.38 ml, 0.38 mmol) in THF was added a solution of (5R,6S)-3-keto-6-phenyl-1-oxa-7-(tert-butoxycarbonyl)aza-spiro[4.5]decane (Preparation 4; 0.105mg, 0.319 mmol) in THF (3 ml). The solution was stirred for 1 hours at −80° C. then a solution of 2-[N,N-bis(trifluoromethylsulfonyl)amino]-5-chloropyridine (0.163 g, 0.415 mmol) in THF (3 ml) was added. The solution was stirred at −80° C. for 30 minutes then at room temperature for 30 minutes before being quenched by addition of saturated ammonium chloride solution and ethyl acetate. The dried ($MgSO_4$) organic phase was purified by chromatography on a column containing silica gel (eluting with hexane containing increasing proportions of ethyl acetate between 0% to 5%). Evaporation of the fractions gave the title compound. $^1$H NMR (360 MHz, $CDCl_3$)δ 7.4 (2H, d, J=7.3 Hz), 7.3–7.22 (3H, m), 6.01 (1H, t, J=2.13 Hz), 5.13 (1H, s), 4.56 and 4.26 (2H, ABdd, J=12.4, 1.97 Hz),4.10 (1H, dt, J=12.6, 4.22 Hz), 3.00 (1H, m), 2.28–2.04 (2H, m), 1.88–1.76 (2H, m), and 1.37 (9H, s). m/z ($ES^+$) 464 (+1).

PREPARATION 6
(5R,6S)-3-Trimethylstannyl-6-phenyl-1-oxa-7-(tert-butoxycarbonyl)aza-spiro[4.5]dec-3-ene To a degassed solution of (5R,6S)-3-trifluoromethylsulfonyloxy-6-phenyl-1-oxa-7-(tert-butoxycarbonyl)aza-spiro[4.5] dec-3-ene (Preparation 5; 0.482 g, 1.04 mmol), lithium chloride (0.264 g, 6.25 mmol), lithium carbonate (0.076 g) and hexamethyl distannane (0.96 g, 2.9 mmol) in THF (10 ml) was added triphenylphosphine palladium (0) (0.06 g). The solution was degassed and then heated at 60° C. for 5 hours under nitrogen. Water (20 ml) and ethyl acetate (20 ml) were added and the dried organic phase was purified by chromatography on a column containing silica gel (eluting with hexane containing increasing proportions of ethyl acetate between 0% to 5%). Evaporation of the fractions gave the title compound as a crystalline solid. $^1$H NMR (360 MHz, $CDCl_3$)δ 7.25 (2H, d, J=7.3 Hz), 7.1–7.0 (3H, m), 5.83 (1H, t, J=2.5 Hz), 4.78 (1H, s), 4.48 and 4.02 (2H, dd, J=12.9, 2.3 Hz), 3.96 (1H, dd, J=6.16, 13.4 Hz), 2.95 (1H, td, J=13.3, 4.5 Hz), 1.84 (1H, m), 1.68 (1H, m), 1.60 (2H, m), 1.19 (9H, s), and 0.0 (6H, s).

PREPARATION 7
(2S,3R)-1-tert-Butoxycarbonyl-3-(3-hydroxypropyn-1-yl)-2-phenylpiperidin-3-ol O-Trimethylsilylpropargyl alcohol (24.51 ml, 20.47 g, 160 ml) was added slowly to a cooled (−10° C.) solution of ethylmagnesium bromide (1M in tetrahydrofuran, 160 ml, 160 mmol). The mixture was stirred at 0° C. for 20 minutes, then at room temperature for 2 hours. The mixture was cooled to −10° C. and a solution of (2S)-1-tert-butoxycarbonyl-2-phenylpiperidin-3-one (Preparation 1; 42.3 g) in tetrahydrofuran (200 ml) was added dropwise over 30 minutes. (Internal temperature below −5° C.). The mixture was stirred at room temperature for 14 hours, poured into water (300 ml) and saturated aqueous ammonium chloride (300 ml) and extracted with ethyl acetate (2×300 ml). The combined organic fractions were washed with brine (300 ml), dried ($MgSO_4$) and the solvent was evaporated under reduced pressure. The residue was dissolved in ethyl acetate (500 ml) and a solution of tetrabutylammonium fluoride (1M in THF, 160 ml, 160 mmol) was added dropwise. The mixture was stirred at room temperature for 30 minutes, water (300 ml) was added, and the layers were separated. The aqueous layer was extracted with ethyl acetate (2×300 ml) and the combined organic fractions were washed with water (300 ml) and brine (300 ml), dried ($MgSO_4$) and the solvent was evaporated under reduced pressure to give the crude title compound as an orange oil (45 g). The crude material was purified by flash column chromatography on silica gel, eluting with hexane/ethyl acetate (90:10 increasing to 25:75) to give the title compound as an amber oil (32.2 g). $^1$H NMR ($CDCl_3$)δ 7.53–7.55 (2H, m), 7.19–7.35 (3H, m), 5.56 (1H, s), 4.27 (2H, s), 3.99–4.03 (1H, m), 3.25 (1H, br s), 2.77–2.81 (1H, m), 2.77 (1H, br s), 2.12–2.20 (1H, m), 1.91–1.99 (2H, m), 1.77–1.83 (1H, m), and 1.39 (9H, s).

PREPARATION 8
2-Bromo-4-(trifluoromethoxy)phenol

To a cooled (0° C.) solution of 4-trifluoromethoxyphenol (3–5.6 g, 0.2 mol) in chloroform (280 ml) was added dropwise a solution of bromine (32 g, 0.2 mol) in chloroform (50 ml). The solution was stirred at 0° C. for 1 hour and at room temperature for 2 hours. Dichloromethane (200 ml) and water (400 ml) ware added and the organic phase was washed further with water(400 ml), brine (200 ml) and dried ($MgSO_4$). The solvent was removed and the residue was purified by distillation at reduced pressure to give the title compound. $^1$H NMR (250 MHz, $CDCl_3$)δ 7.38 (1H, d, J=2.1 Hz), 7.13 (1H, dd, J=9.1, 2.1 Hz), 7.03 (1H, d, J=9.1 Hz), and 5.53 (1H, s).

PREPARATION 9
2-Benzyloxy-5-(trifluoromethoxy)bromobenzene

2-Bromo-4-(trifluoromethoxy)phenol (Preparation 8; 5 g, 20 mmol) was dissolved in N,N-dimethylformamide (60 ml), and potassium carbonate (5.4 g, 40 mmol) was added, followed by benzyl bromide (3.5 ml. 30 mmol), and the reaction was stirred at ambient temperature for 15 hours. The reaction was diluted with water (150 ml) and extracted into ethyl acetate (3×60 ml). The combined organic fractions were washed with water (100 ml), brine (100 ml), dried ($MgSO_4$) and evaporated in vacuo. Purification on silica, eluting with 2% and 5% ethyl acetate in hexane gave the title compound as a clear oil (6.7 g, 96%). $^1$H NMR (250 MHz, $CDCl_3$)δ 5.47 (2H, s), 7.23 (1H, d, J=9 Hz), 7.43 (1H, dd J=8.2, 2.9 Hz), and 7.75 (6H, m).

PREPARATION 10
Z-(2S,3R)-1-tert-Butoxycarbonyl-3-(3-hydroxyprop-1-en-1-yl)-2-phenylpiperidin-3-ol Palladium on calcium carbonate, poisoned with lead (Lindlar catalyst, 2 g) was added to a solution of (2S,3R)-

1-tert-butoxycarbonyl-3-(3-hydroxypropyn-1yl)-2-phenylpiperidin-3-ol (Preparation 7; 32 g, 96.6 mmol) in ethyl acetate (300 ml) and the mixture was stirred under hydrogen (1 atmosphere) for 4 hours. The mixture was filtered and the solvent was evaporated under reduced pressure to give the title compound as an oil to (32 g, 100%). $^1$H NMR (360 MHz, CDCl$_3$)δ 7.42 (2H, d, J=7.6 Hz), 7.35–7.25 (3H, m), 5.83 (1H, d, J=12.3 Hz), 5.68 (1H, dt, J=12.3, 6.0 Hz), 5.06 (1H, s), 4.27 (1H, m), 4.12 (2H, m), 3.32 (1H, m), 3.13 (1H, s), 2.28 (1H, t, J=5.9 Hz), 2.02 (1H, m), 1.92–1.78 (3H, m), and 1.32 (9H, s). m/z (ES$^+$) 334 (M+1).

PREPARATION 11
(5R,6S)-6-Phenyl-1-oxa-7-(tert-butoxycarbonyl)aza-spiro[4.5]dec-3-ene Diethylazodicarboxylate (18.2 ml, 116 mmol) in THF (100 ml) was added dropwise to a solution of Z-(2S,3R)-1-tert-butoxycarbonyl-3-(3-hydroxyprop-1-en-1-yl)-2-phenylpiperidin-3-ol (Preparation 10; 32 g, 96 mmol) and triphenylphosphine (30.2 g, 115 mmol) in THF (700 ml). The mixture was stirred at 0° C. for 30 minutes then at room temperature for 1.5 hours. The solvent was evaporated under reduced pressure and the residue was purified by flash column chromatography on silica gel, eluting with hexane/ethyl acetate (95:5 increasing to 80:20) to give the title compound as a colorless solid (23.4 g, 77%). $^1$H NMR (CDCl$_3$)δ 7.45 (2H, d, J=7.4 Hz), 7.27 (2H, t, J=7.4 Hz), 7.20 (1H, t, J=7.4 Hz), 6.03 (1H, dt, J=6.1, 2.0 Hz), 5.68 (1H, dt, J=6.1, 2.0 Hz), 5.06 (1H, s), 4.61 (1H, dt, J=13.1, 2.0 Hz), 4.32 (1H, dt, J=13.1, 2.0 Hz), 4.08 (1H, m), 3.05 (1H, m), 2.05 (1H, m), 1.75 (3H, m), and 1.37 (9H, s). m/z (ES$^+$) 316 (M+1).

PREPARATION 12
2-Benzyloxy-5-(trifluoromethoxy)benzene

Benzyl bromide (66.17 ml, 95.35 g, 0.56 mol) was added to a mixture of 4-(trifluoromethoxy)phenol (90.26 g, 0.51 mol) and potassium carbonate (140.97 g, 1.2 mol) in dimethylformamide (160 ml) and the mixture was stirred at room temperature for 72 hours. The mixture was poured into water (1.5 l) and extracted with ethyl acetate (3×500 ml). The combined organic fractions were washed with aqueous sodium carbonate (saturated, 500 ml), dried (MgSO$_4$) and the solvent was evaporated under reduced pressure to give the title compound as a colorless solid (133.5 g, 99%). $^1$H NMR (360 MHz, CDCl$_3$) d 7.39 (5H, m), 7.14 (2H, d, J=9.0 Hz), 6.95 (2H, d, J=9.0 Hz), and 5.05 (2H, s).

PREPARATION 13
2-Benzyloxy-5-(trifluoromethoxy)iodobenzene

Iodine (71.96 g, 0.28 mol) in chloroform was added dropwise to a mixture of 2-benzyloxy-5-(trifluoromethoxy) benzene (Preparation 12, 73.06 g, 0.27 mol) and silver trifluoroacetate (71.57 g, 0.32 mol) in dichloromethane and the mixture was stirred at room temperature for 18 hours. The mixture was filtered through celite, washed with aqueous sodium thiosulfate (5%, 2×2 l), dried (MgSO$_4$) and the solvent was evaporated under reduced pressure. The residue was purified by flash column chromatography on silica gel, eluting with hexane/ethyl acetate, to give the title compound as a colorless oil (108.03 g), containing 11% unreacted 2-benzyloxy-5-(trifluoromethoxy)iodobenzene. $^1$H NMR (360 MHz, CDCl$_3$) d 7.67 (1H, d, J=2.8 Hz), 7.40 (5H, m), 7.16 (1H, dd, J=8.9, 2.8 Hz), 6.82 (1H, d, J=8.9 Hz), and 5.14 (2H, s).

PREPARATION 14
(5R,6S)-3-(2-Benzyloxy-5-(trifluoromethoxy)phenyl)-6-phenyl-1-oxa-7-(tert-butoxycarbonyl)aza-spiro[4.5]dec-3-ene (5R,6S)-3-Trimethylstannyl-6-phenyl-1-oxa-7-(tert-butoxycarbonyl)aza-spiro[4.5]dec-3-ene (Preparation 6; 6.43 mmol), lithium chloride (0.163 g), benzyloxy-5-(trifluoromethoxy)phenol (Preparation 9; 7.7 mmol) in toluene (25 ml) was degassed before addition of triphenylphosphine palladium (0) (0.37 g). The solution was degassed thoroughly before heating to 110° C. for 14 hours. The solution was partitioned between water and ethyl acetate and the dried organic phase was purified by chromatography on a column containing silica gel (eluting with hexane containing increasing proportions of ethyl acetate between 0% to 4%) to give the title compound. $^1$H NMR (360 MHz, CDCl$_3$)δ 1.33 (9H, s), 1.65 (1H, m), 1.76 (2H, m), 2.08 (1H, m), 3.11 (1H, m), 4.08 (1H, m), 4.60 (1H, dd, J=12.2 Hz, J=2 Hz), 4.92 (1H, dd, J=12.1 Hz, J=1.8 Hz), 5.08 (1H, s), 5.1 (2H, q, J=11.5 Hz), 6.65 (1H, s), 6.94 (2H, d, J=8.9 Hz), 7.08 (1H, d, J=9 Hz), 7.18 (2H, t, J=8.1 Hz), 7.25 (3H, m), 7.38 (5H, m).

PREPARATION 15
(3S,5R,6S)-3-(2-Hydroxy-5-(trifluoromethoxy)phenyl)-6-phenyl-1-oxa-7-(tert-butoxycarbonyl)aza-spiro[4.5]decane (5R,6S)-3-(2-Benzyloxy-5-(trifluoromethoxy)phenyl)-6-phenyl-1-oxa-7-(tert-butoxycarbonyl)aza-spiro[4.5]dec-3-ene (Preparation 14) (3.88 g) was dissolved in ethyl acetate (15 ml) and methanol (15 ml). Palladium hydroxide on carbon (1.00 g) was added and the suspension was shaken under a hydrogen atmosphere (50 psi) for 72 hours. The mixture was filtered and the solvent was evaporated under reduced pressure. The residue was purified by medium pressure chromatography on silica gel, eluting with hexane/ethyl acetate (75:25) to give (3R,5R,6S)-3-(2-hydroxy-5-(trifluoromethoxy)phenyl)-6-phenyl-1-oxa-7-(tert-butoxycarbonyl)aza-spiro[4.5]decane (191 mg), $^1$H NMR (250 MHz, CDCl$_3$)δ 7.70 (2H, d, J=7.3 Hz), 7.33 (2H, t, J=7.3 Hz), 7.26 (1H, d, J=7.3 Hz), 7.05 (1H, br s), 6.96 (2H, m), 6.82 (1H, d, J=9.4 Hz), 5.43 (1H, s), 4.27 (1H, m), 4.01 (1H, m), 3.95 (1H, m), 3.73 (1H, m), 2.73 (2H, m), 2.33 (1H, m), 1.87–1.58 (4H, m); and 1.50 (9H, s) and (3S,5R,6S)-3-(2-hydroxy-5-(trifluoromethoxy)phenyl)-6-phenyl-1-oxa-7-(tert-butoxycarbonyl)aza-spiro[4.5]decane (2.3 g), $^1$H NMR (360 MHz, CDCl$_3$) 5 1.38 (9H, s), 1.73 (2H, m), 1.81 (1H, m), 2.18 (2H, m), 2.50 (1H, m), 2.81 (1H, m), 3.62 (1H, t, J=7.2 Hz), 3.92 (1H, m), 3.98 (1H, d, J=13.2 Hz), 4.23 (1H, m), 5.33 (1H, s), 6.75 (1H, d, J=8.5 Hz), 6.94 (2H, m), 7.25 (1H, m), 7.31 (2H, m), and 7.55 (2H, d, J=7.8 Hz).

PREPARATION 16
(3R,5R,6S)-3-(2-Benzyloxy-5-(trifluoromethoxy)phenyl)-6-phenyl-1-oxa-7-(tert-butoxycarbonyl) aza-spiro[4.5]decane A mixture of 2-benzyloxy-5-(trifluoromethoxy)iodobenzene (Preparation 13, 21.8 g, 55.2 mmol), (5R,6S)-6-phenyl-1-oxa-7-(tert-butoxycarbonyl)aza-spiro[4.5]dec-3-ene (Preparation 11, 7.0 g, 22.1 mmol), tetra-n-butylammonium chloride (6.18 g, 22.2 mmol), lithium chloride (9.35 g, 0.22 mol) and potassium formate (5.64 g, 67.0 mmol) in dimethylformamide (100 ml) was degassed with a firestone valve (5×). Palladium acetate (491 mg, 2.2 mmol) was added and the mixture was degassed with a firestone valve (5×). The mixture was stirred at 60° C. for 15 hours, then further 2-benzyloxy-5-(trifluoromethoxy)iodobenzene (Preparation 13, 4.32 g, 11.0 mmol), potassium formate (2.78 g, 33.5 mmol) and palladium acetate (260 mg, 1.1 mmol) were added. The mixture was stirred at 60° C. for 22 hours, cooled and filtered. The solvent was evaporated under reduced pressure, water (600 ml) was added and the mixture was extracted with ethyl acetate (2×300 ml). The combined organic fractions were washed with brine (300 ml), dried (MgSO₄) and the solvent was evaporated under reduced pressure. The residue was purified by flash column chromatography on silica gel, eluting with hexane/ dichloromethane (75:25 increasing to 0:100) then dichloromethane/ethyl acetate (95:5), to give the title compound (9.42 g, 73%). ¹H NMR (360 MHz, CDCl₃) d 7.56 (2H, d, J=7.7 Hz), 7.40–7.20 (8H, m), 7.14 (1H, d, J=2.0 Hz), 7.00 (1H, dd, J=8.9, 2.0 Hz), 6.88 (1H, d, J=8.9 Hz), 5.30 (1H, s), 5.08 (2H, s), 4.27 (1H, m), 3.97 (1H, m), 3.87 (2H, m), 2.78 (1H, m), 2.56 (1H, m), 2.15 (1H, m), 1.96 (1H, m), 1.67 (3H, m), and 1.42 (9H, s).

PREPARATION 17
(3R,5R,6S)-3-(2-Hydroxy-5-(trifluoromethoxy)phenyl)-6-phenyl-1-oxa-7-(tert-butoxycarbonyl)aza-sliro[4.5]decane Palladium on carbon (10%, 0.59 g) was added to a solution of (3R,5R,6S)-3-(2-benzyloxy-5-(trifluoromethoxy)phenyl)-6-phenyl-1-oxa-7-(tert-butoxycarbonyl)aza-spiro[4.5]decane (Preparation 16, 6.10 g, 10.5 mmol) in methanol-water (99:1, 200 ml) and the mixture was stirred under hydrogen (50 psi.) for 72 hours. The mixture was filtered, washing with ethanol, and the solvent was evaporated under reduced pressure.

The residue was purified by flash column chromatography on silica gel, eluting with dichloromethane/ethyl acetate (99:1 increasing to 90:10) to give the title compound. ¹H NMR (360 MHz, CDCl₃) d 7.70 (2l1, d, J=7.3 Hz), 7.33 (2H, t, J=7.3 Hz), 7.26 (1H, d, J=7.3 Hz), 7.05 (1H, br s), 6.96 (2H, m), 6.82 (1H, d, J=9.4 Hz), 5.43 (1H, s), 4.27 (1H, m), 4.01 (1H, m), 3.95 (1H, m), 3.73 (1H, m), 2.73 (2H, m), 2.33 (1H, m), 1.87–1.58 (4H, m), and 1.50 (9H, s).

PREPARATION 18
(3S,5R,6S)-3-[2-(1-Phenylthiocycloprop-1-yl)oxy-5-(trifluoromethoxy)phenyl]-6-phenyl-1-oxa-7-(tert-butoxycarbonyl)aza-spiro[4.5]decane (3 S,5R,6S)-3-(2-Hydroxy-5-(trifluoromethoxy)phenyl)-6-phenyl 1-oxa-7-(tert-butoxycarbonyl)aza-spiro[4.5] decane (Preparation 15) (290 mg, 0.59 mmol) was dissolved in toluene (5 ml) and silver carbonate (179 mg, 0.65 mmol) was added in one portion. (1-Iodocycloprop-1-yl) phenylsulfide (Cohen T. and Matz J. R., *J. Am. Chem. Soc.* 1980, 102, 6902) (180 mg, 0.65 mmol) was then added over one minute at room temperature. The mixture was stirred at 55° C. for 4 hours, then further portions of silver carbonate (179 mg, 0.65 mmol) and (1-iodocycloprop-1-yl) phenylsulfide (180 mg, 0.65 mmol) were added. The mixture was stirred at 55° C. for a further 3 hours, cooled, filtered and the solvent was evaporated under reduced pressure. The residue was purified by column chromatography on silica gel, eluting with hexane/ethyl acetate (90:10 increasing to 80:20) to give the title compound as a colourless oil (120 mg, 32%). ¹H NMR (250 MHz, CDCl₃) δ 7.55–7.44 (4H, m), 7.36–7.23 (7H, m), 7.13–7.02 (2H, m), 5.16 (1H, br s), 4.09 (1H, t, J=6 Hz), 4.03–3.92 (1H, m), 3.67–3.49 (2H, m), 2.94–2.79 (1H, m), 2.26 (1H, dd, J=7.9, 12.9 Hz), 2.15–2.01 (2H, m), 1.76–1.59 (3H, m), 1.53–1.45 (4H, m), and 1.36 (9H, s). m/z (ES⁺) 642 (M+1).

PREPARATION 19
(3R, 5R,6S)-3-[2-(1-Phenylthiocycloprop-1-yl)oxy-5-(trifluoromethoxy)phenyl]-6-phenyl-1-oxa-7-(tert-butoxycarbonyl)aza-spiro[4.5]decane Prepared from (3R,5R,6S)-3-(2-hydroxy-5-(trifluoromethoxy)phenyl)-6-phenyl-1-oxa-7-(tert-butoxycarbonyl)aza-spiro[4.5]decane (Preparation 17) according to the method of Preparation 18. ¹H NMR (360 MHz, CDCl₃)δ 7.57 (2H, app. d, J=7.6 Hz), 7.45 (2H, app. d, J=7.7 Hz), 7.36–7.19 (7H, m), 7.16–7.06 (2H, m), 5.28 (1H, br s), 4.13 (1H, app. t, J=7.8 Hz), 3.96 (1H, br. d, J=13 Hz), 3.80–3.60 (2H, m), 2.79 (1H, br. t, J=13 Hz), 2.50 (1H, dd, J=13, 7.9 Hz), 2.17 (1H, dt, J=13, 4.6 Hz), 1.80 (1H, dd, J=12, 9.8 Hz), 1.75–1.38 (7H, m), and 1.44 (9H, s). m/z (ES⁺) 642 (M+1).

PREPARATION 20
(3S 5R, 6S)-3-[2-Cyclopropoxy-5-(trifluoromethoxy) phenyl]-6-phenyl-1-oxa-7-(tert-butoxycarbonyl)aza-spiro [4.5]decane Naphthalene (120 mg, 0.936 mmol) was dissolved in THF (1.5 ml) under nitrogen and freshly cut lithium metal (7.0 mg, 0.94 mmol) was added. The mixture was then sonicated at room temperature for 20 minutes to produce a dark green solution of lithium naphthalenide. This solution was cooled to −78° C., then (3S,5R,6S)-3-[2-(1-phenylthiocycloprop-1-yl)oxy-5-(trifluoromethoxy)phenyl]-6-phenyl-1-oxa-7-(tert-butoxycarbonyl)aza-spiro[4.5]decane (Preparation 18) (120 mg, 0.187 mmol) in THF (0.5 ml) was added over 1 minute. The reaction mixture was stirred for 30 minutes, then water (5 ml) and ether (10 ml) were added. The layers were separated and the aqueous layer was extracted with ether (10 ml). The combined organic fractions were dried (MgSO₄) and the solvent was evaporated under reduced pressure. The residue was purified by column chromatography on silica gel, eluting with hexane/ethyl acetate (90:10 increasing to 80:20) to give the title compound as a colourless oil (58.6 mg, 59%). ¹H NMR (250 MHz, CDCl₃)δ 7.58–7.52 (2H, m), 7.36–7.17 (4H, m), 7.10–7.01 (2H, m), 5.18 (1H, br s), 4.20 (1H, t, J=6.7 Hz), 4.05–3.95 (1H, m), 3.76–3.55 (3H, m), 2.92–2.79 (1H, m), 2.37 (1H, dd, J=12.9, 7.8 Hz), 2.18–2.06 (2H, m), 1.80–1.67 (3H, m), 1.38 (9H, s), and 0.86–0.73 (4H, m). m/z (ES⁺) 534 (M+1).

PREPARATION 21
(3R,5R,6S)-3-[2-Cyclopropoxy-5-(trifluoromethoxy) phenyl]-6-phenyl-1-oxa-7-(tert-butoxycarbonyl)aza-spiro [4.5]decane Naphthalene (120 mg, 0.936 mmol) was dissolved in THF (1.5 ml) under nitrogen and freshly cut lithium metal (7.0 mg, 0.94 mmol) was added. The mixture was then sonicated at room temperature for 20 minutes to produce a dark green solution of lithium naphthalenide. A solution of (3R,5R,6S)-3-[2-(1-phenylthiocycloprop-1-yl)oxy-5-(trifluoromethoxy) phenyl]-6-phenyl-1-oxa-7-(tert-butoxycarbonyl)aza-spiro [4.5]decane (Preparation 19, 135 mg, 0.21 mmol) in THF (2 ml) under nitrogen was cooled to −78° C. and the solution of lithium naphthalenide in THF was added dropwise until the intense green colour persisted. The reaction was then stirred for one minute, water (5 ml) was added and the mixture was warmed to room temperature. Ether (10 ml) was added and the layers were separated. The aqueous phase was extracted with a further portion of ether (10 ml) and the combined organic phases were dried (MgSO₄) and the solvent was evaporated under reduced pressure. The residue was purified by column chromatography on silica gel, eluting with hexane/ethyl acetate (50:50) to give the title compound as a colourless oil (87 mg, 78%). ¹H NMR (360 MHz, CDCl₃)δ 7.59 (2H, app. d, J=7.6 Hz), 7.32 (2H, app. t, J=7.6 Hz), 7.27–7.18 (2H, m), 7.11–7.03 (2H, m), 5.32 (1H, br s), 4.29–4.21 (1H, m), 3.97 (1H, br. d, J=13 Hz), 3.83–3.68 (3H, m), 2.76 (1H, dt, J=13, 4.1 Hz), 2.55 (1H, dd, J=13, 7.2 Hz), 2.22 (1H, dt, J=12, 5.2 Hz), 1.85 (1H, dd, J=13, 9.9 Hz), 1.80–1.63 (3H, m), 1.46 (9H, s), and 0.82–0.76 (4H, m). m/z (ES⁺) 534 (M+1).

COMPOUND A
(3S 5R, 6S)-3-[2-Cyclopropoxy-5-(trifluoromethoxy) phenyl]-6-phenyl-1-oxa-7-aza-sipiro[4.5]decane Hydrochloride Trifluoroacetic acid (2.5 ml) was added dropwise to a stirred, cooled 0° C.) solution of (3S,5R,6S)-3-[2-cyclopropoxy-5-(trifluoromethoxy)phenyl]-6-phenyl-1-oxa-7-(tert-butoxycarbonyl)aza-spiro[4.5]decane (Preparation 20; 492 mg, 0.92 mmol) in dichloromethane (25 ml) and the mixture was stirred at room temperature for 3 hours. The mixture was poured into water (50 ml), the pH was adjusted to 10.0 with aqueous sodium hydroxide (4M) and the mixture was extracted with dichloromethane (3×50 ml). The combined organic fractions were dried (MgSO$_4$) and the solvent was evaporated under reduced pressure. The residue was purified by flash column chromatography on silica gel, eluting with dichloromethane/methanol/ammonia (aq.) (96:4:0.4 increasing to 94:6:0.6). The residue was dissolved in ethanol (20 ml), cooled in ice and ethereal hydrogen chloride (1M, 1.8 ml, 1.8 mmol) was added dropwise. The mixture as stirred at 0° C. for 5 minutes, then the solvent was evaporated under reduced pressure. The residue was crystallized from ether (20 ml)/ethanol (0.5 ml) and the solid was collected and dried in vacuo to give the title compound as a colorless solid (354 mg, 89%). m.p. 214–216° C., $^1$H NMR (500 MHz, CD$_3$OD)δ 7.59 (2H, m), 7.52 (3H, z), 7.26 (1H, d, J=8.9 Hz), 7.03 (1H, dd, J=8.9, 2.2 Hz), 6.20 (1H, d, J=2.2 Hz), 4.85 (2H, hr s), 4.43 (1H, s), 4.19 (1H, t, J=8.0 Hz), 3.87 (1H , quin, J=8.0 Hz), 3.76 (1H, m), 3.44 (1H, m), 3.25 (2H, m) 2.29–1.78 (6H, m), 0.80 (2H, m), and 0.66 (2H, m). m/z (ES$^+$) 434 (M+1). Found: C, 61.41; H, 5.51; N, 3.08. C$_{24}$H$_{26}$F$_3$NO$_3$ . HCl requires: C, 61.34; H, 5.79; N, 2.98%.

COMPOUND B
(3R,5R,6S)-3-[2-Cyclopropoxy-5-(trifluoromethoxy) phenyl]-6phenyl-1-oxa-7-aza-spiro[4.5]decane Prepared from the compound of Preparation 21 according to the method used for Compound A. $^1$H NMR (360 MHz, CDCl$_3$)δ 7.50–7.42 (2H, m), 7.36–7.26 (3H, m), 7.03 (1H, d, J=8.9 Hz), 6.95 (1H, hr. d, J=8.9 Hz), 6.81 (1H, hr s), 3.92 (1H, t, J=7.4 Hz), 3.62–3.53 (2H, m), 3.50 (1H, s), 3.20 (1H, dd, J—12, 4.2 Hz), 2.77 (1H, dt, J=12, 2.8 Hz), 2.30–1.93 (4H, m), 1.87 (1H, hr s), 1.71–1.49 (3H, m), 0.76–0.65 (2H, m), and 0.65–0.54 (2H, m). m/z (ES$^+$) 434 (M+1).

Particularly preferred NK-1 receptor antagonists of use in the present invention are compounds which are potent NK-1 receptor antagonists, i.e. compounds with an NK-1 receptor affinity (IC$_{50}$) of less than 10 nM, favourably less than 2 nM and preferably less than 1 nM.

The class of orally active, long acting, CNS-penetrant NK-1 receptor antagonists of use in the present invention is identified using a combination of the following assays:

Assay 1: NK-1 Receptor binding

NK-1 receptor binding assays are performed in intact Chinese hamster ovary (CHO) cells expressing the human NK-1 receptor using a modification of the assay conditions described by Cascieri et al, *J. Pharmacol. Exp. Ther.*, 1992, 42, 458. The receptor is expressed at a level of 3×10$^5$ receptors per cell. Cells are grown in monolayer culture, detached from the plate with enzyme-free dissociation solution (Speciality Media Inc.), and washed prior to use in the assay. $^{125}$I-Tyr$^8$-substance P (0.1 nM, 2000 Ci/mmol; New England Nuclear) is incubated in the presence or absence of test compounds (dissolved in 5 μl dimethylsulphoxide, DMSO) with 5×10$^4$ CHO cells. Ligand binding is performed in 0.25 ml of 50 mM Tris-HCl, pH7.5, containing 5 mM MnCl$_2$, 150 mM NaCl, 0.02% bovine serum albumin (Sigma), 50 μg/ml chymostatin (Peninsula), 0.1 nM phenyl-methylsulphonyl fluoride, 21 g/ml pepstatin, 2 μg/ml leupeptin and 2.8 μg/ml furoyl saccharine. The incubation proceeds at room temperature until equilibrium is achieved (>40 minutes) and the receptor-ligand complex is harvested by filtration over GF/C filters pre-soaked in 0.1% polyethylenimine using a Tomtek 96-well harvester. Non-specific binding is determined using excess substance P (1 μM) and represents <10% of total binding.

assay 2: Gerbil Foot-Tapping

CNS penetrant NK-1 receptor antagonists for use in the present invention can be identified by their ability to inhibit foot tapping in gerbils induced by central infusion of NK-1 receptor agonists such as GR73632 based on the method of Rupniak & Williams, *Eur. J. Pharmacol.*, 1994, 265, 179.

Briefly, male or female Mongolian gerbils (35–70 g) are anaesthetised by inhalation of an isoflurane/oxygen mixture to permit exposure of the jugular vein in order to permit administration of test compounds or vehicle in an injection volume of 5 ml/kg i.v. Alternatively, test compounds may be administered orally or by subcutaneous or intraperitoneal routes. A skin incision is then made in the midline of the scalp to expose the skull. A selective NK-1 receptor agonist (e.g. GR$^{73632}$ (d Ala[L-Pro$^9$,Me-Leu$^{10}$]-substance P-(7–11)) is infused directly into the cerebral ventricles (e.g. 3 pmol in 5 μl i.c.v., depending on test substance) by vertical insertion of a cuffed 27 gauge needle to a depth of 4.5 mm below bregma. The scalp incision is closed and the animal allowed to recover from anaesthesia in a clear perspex observation box (25 cm×20 cm×20 cm). The-duration of hind foot tapping is then recorded continuously for approximately 5 minutes.

Assay 3: Ferret Emesis

Individually housed male ferrets (1.0–2.5 kg) are dosed orally by gavage with test compound. Ten minutes later they are fed with approximately 100 g of tinned cat food. At 60 minutes following oral dosing, cisplatin (10 mg/kg) is given i.v. via a jugular vein catheter inserted under a brief period of halothane anaesthesia. The catheter is then removed, the jugular vein ligated and the skin incision closed. The ferrets recover rapidly from the anaesthetic and are mobile within 10–20 minutes. The animals are observed continuously during recovery from the anaesthetic and for 4 hours following the cisplatin injection. The numbers of retches and vomits occurring during the 4 hours after cisplatin administration are recorded by trained observers.

Assay 4: Separation-Induced Vocalisation

Male and female guinea-pigs pups are housed in family groups with their mothers and littermates throughout the study. Experiments are commenced after weaning when the pups are 2 weeks old. Before entering an experiment, the pups are screened to ensure that a vigorous vocalisation response is reproducibly elicited following maternal separation. The pups are placed individually in an observation cage (55 cm×39 cm×19 cm) in a room physically isolated from the home cage for 15 minutes and the duration of vocalisation during this baseline period is recorded. Only animals which vocalise for longer than 5 minutes are employed for drug challenge studies (approximately 50% of available pups may fail to reach this criterion). On test days each pup receives an oral dose or an s.c. or i.p. injection of test compound or vehicle and is then immediately returned to the home cage with its mother and siblings for 30 to 60 minutes before social isolation for 15 minutes as described above. The duration of vocalisation on drug treatment days is expressed as a percentage of the pre-treatment baseline value for each animal. The same subjects are retested once weekly for up to 6 weeks. Between 63 and 8 animals receive each test compound.

As used herein, the term "CNS-penetrant" refers to NK-1 receptor antagonists which are able to inhibit NK-1 receptor antagonist-induced foot-tapping in the gerbil as hereinafter defined.

Essentially, hind foot-tapping in the gerbil induced by infusion of the NK-1 receptor agonist, $GR^{73632}$ (d Ala[L-Pro$^9$,Me-Leu$^{10}$]-substance P-(7–11)), under anaesthesia, directly into the central ventricles is inhibited when a CNS-penetrant NK-1 receptor antagonist is administered intravenously immediately prior to $GR^{73632}$ challenge, wherein hind foot-tapping over a period of five minutes following recovery from the anaesthesia is inhibited with an $ID_{50} \leq 3$ mg/kg, and preferably with an $ID_{50} \leq 1$ mg/kg.

In an alternative method, the NK-1 receptor antagonist is administered orally, 1 hour prior to $GR^{73632}$ challenge, wherein the foot-tapping over a period of five minutes following recovery from anaesthesia is inhibited with an $ID_{50} \leq 30$ mg/kg, and preferably with an $ID_{50} \leq 10$ mg/kg CNS-penetrant NK-1 receptor antagonists of use in the present ivnention are also effective in the attenuation of separation-induced vocalisations by guinea-pig pups as hereinafter defined.

Essentially, a vocalisation response in guinea-pig pups is induced by isolation from their mothers and littermates, which response is attenuated when a CNS-penetrant NK-1 receptor antagonist is administered subcutaneously 30 minutes prior to isolation, wherein vocalisations during the first 15 minutes of isolation are attenuated with an $ID_{50} \leq 20$ mg/kg, preferably with an $ID_{50} \leq 10$ mg/kg, and especially with an $ID_{50} \leq 5$ mg/kg.

In an alternative method, the NK-1 receptor antagonist is administered orally, 4 hours prior to isolation, wherein vocalisations during the first 15 minutes of isolation are attenuated with an $ID_{50} \leq 20$ mg/kg, preferably with an $ID_{50} \leq 10$ mg/kg, and especially with an $ID_{50} \leq 5$ mg/kg.

A suitable selection cascade for $NK_1$ antagonists of use according to the present invention is as follows:

(i) Determine affinity for human $NK_1$ receptor in radio-ligand binding studies (Assay 1); select compounds with $IC_{50} \leq 10$ nM. preferably $IC_{50} \leq 2$ nM, especially $IC_{50} \leq 1$ nM.

(ii) Determine ability of compounds to penetrate CNS by their ability to inhibit foot tapping in gerbils induced by central injection of an $NK_1$ agonist (Assay 2); select compounds that inhibit foot tapping with $ID_{50} \leq 3$ mg/kg i.v., and preferably $ID_{50} \leq 1$ mg/kg i.v. when administered immediately prior to central $NK_1$ agonist challenge, or $ID_{50} \leq 30$ mg/kg p.o., and preferably $ID_{50} \leq 10$ mg/kg p.o. 1 hour prior to challenge.

(iii) Determine central duration of action of compounds in gerbil foot tapping assay following intravenous administration 24 hours prior to central $NK_1$ agonist challenge; select compounds showing $\leq 25$-fold loss of potency compared with $ID_{50}$ determined in step (ii) above with the proviso that $ID_{50} \leq 10$ mg/kg i.v., and preferably $\leq 5$ mg/kg i.v. after 24 hour pre-treatment.

(iv) Determine oral bioavailability of compounds by pharmacokinetic analysis, activity in gerbil foot tapping assay following oral administration and/or by ability to inhibit cisplatin-induced emesis in ferrets (Assay 3); select compounds with $ID_{90} \leq 3$ mg/kg p.o., and preferably $ID_{90} \leq 1$ mg/kg p.o.

Particularly preferred compounds of use in the present invention are identified using steps (i) to (iv) followed by step (v):

(v) Determine activity of compounds in assays sensitive to conventional antipsychotic drugs (inhibition of distress vocalisations in guinea-pig pups (Assay 4)). Select compounds with $ID_{50} \leq 20$ mg/kg, and preferably $ID_{50} \leq 10$ mg/kg.

Yet further preferred compounds of use in the present invention may be selected from those compounds which satisfy the NK-1 receptor binding criteria of step (i) which, in addition, have $\leq 5$-fold shift in affinity when incubated in the presence of human serum albumin (HSA) to show non-specific protein binding.

One example of a NK-1 receptor antagonist of use in the present invention is the compound 2-(R)-(1-(R)-(3,5-bis (trifluoromethyl)phenyl)-ethoxy)-3-(S)-(4-fluorophenyl)-4-(3-(5-oxo-1H,4H-1,2,4-triazolo)methyl)-morpholine, the preparation of which is described in International Patent Specification No. WO 95/16679. In the aforementioned assays, this compound has the following activity:

human NK-1 receptor binding: $IC_{50} = 0.1$ nM gerbil foot-tapping (5 mins.): $ID_{50} = 0.36$ mg/kg i.v.

gerbil foot-tapping (24 hrs.): $ID_{50} = 0.33$ mg/kg i.v.

ferret emesis: $ID_{90} < 3$ mg/kg p.o.

The following example illustrates pharmaceutical compositions according to the invention.

EXAMPLE 1 Tablets containing 50–300 mg of NK-1 antagonist

|  | Amount mg | | |
|---|---|---|---|
| NK-1 antagonist | 50.0 | 100.0 | 300.0 |
| Microcrystalline cellulose | 80.0 | 80.0 | 80.0 |
| Modified food corn starch | 80.0 | 80.0 | 80.0 |
| Lactose | 189.5 | 139.5 | 139.5 |
| Magnesium Stearate | 0.5 | 0.5 | 0.5 |

The active ingredient, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the NK-1 receptor antagonist per tablet.

EXAMPLE 2 Parenteral injection

|  | Amount | |
|---|---|---|
| Active Ingredient | 10 to 300 | mg |
| Citric Acid Monohydrate | 0.75 | mg |
| Sodium Phosphate | 4.5 | mg |
| Sodium Chloride | 9 | mg |
| Water for injection | to 10 | ml |

The sodium phosphate, citric acid monohydrate and sodium chloride are dissolved in a portion of the water. The active ingredient is dissolved or suspended in the solution and made up to volume.

Pharmaceutical compositions comprising a combination of a NK-1 receptor antagonist and an antipsychotic agent may be prepared with separate active ingredients or with a combination of active ingredients in one composition. In such combined preparations, the ratio of the NK-1 receptor antagonist and the antipsychotic agent will depend upon the choice of active ingredients.

EXAMPLE 3 Tablets containing 50–300 mg of NK-1 antagonist and 5–10 mg of haloperidol

| | Amount mg | | | | | |
|---|---|---|---|---|---|---|
| NK-1 antagonist | 50.0 | 50.0 | 100.0 | 100.0 | 300.0 | 300.0 |
| haloperidol | 5.0 | 10.0 | 5.0 | 10.0 | 5.0 | 10.0 |
| Microcrystalline cellulose | 80.0 | 80.0 | 80.0 | 80.0 | 80.0 | 80.0 |
| Modified food corn starch | 80.0 | 80.0 | 80.0 | 80.0 | 80.0 | 80.0 |
| Lactose | 184.5 | 179.5 | 134.5 | 129.5 | 134.5 | 129.5 |
| Magnesium Stearate | 0.5 | 0.5 | 0.5 | 0.5 | 0.5 | 0.5 |

EXAMPLE 4 Tablets containing 50–300 mg of NK-1 antagonist and 25 mg of chlorpromazine hydrochloride

| | Amount mg | | |
|---|---|---|---|
| NK-1 antagonist | 50.0 | 100.0 | 300.0 |
| chlorpromazine hydrochloride | 25.0 | 25.0 | 25.0 |
| Microcrystalline cellulose | 80.0 | 80.0 | 80.0 |
| Modified food corn starch | 80.0 | 80.0 | 80.0 |
| Lactose | 164.5 | 114.5 | 114.5 |
| Magnesium Stearate | 0.5 | 0.5 | 0.5 |

The active ingredients, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the CNS-penetrant NK-1 receptor antagonist per tablet.

We claim:

1. A method for the treatment or prevention of mania or hypomania, which method comprises the administration to a patient in need of such treatment of an effective amount of an NK-1 receptor antagonist which is selected from:

(3S,5R,6S)-3-[2-cyclopropoxy-5-(trifluoromethoxy) phenyl]-6-phenyl-1-oxa-7-aza-spiro[4.5]decane; and (3R,5R,6S)-3-[2-cyclopropoxy-5-(trifluoromethoxy) phenyl]-6-phenyl-1-oxa-7-aza-spiro[4.5]decane;

or a pharmaceutically acceptable salt thereof.

2. A method for the treatment or prevention of mania or hypomania, which method comprises the administration to a patient in need of such treatment of an amount of an NK-1 receptor antagonist and an amount of an antipsychotic agent, such that together they give effective relief, wherein the NK-1 receptor antagonist is selected from:

(3S,5R,6S)-3-[2-cyclopropoxy-5-(trifluoromethoxy) phenyl]-6-phenyl-1-oxa-7-aza-spiro[4.5]decane; and (3R,5R,6S)-3-[2-cyclopropoxy-5-(trifluoromethoxy) phenyl]-6-phenyl-1-oxa-7-aza-spiro[4.5]decane;

or a pharmaceutically acceptable salt thereof.

* * * * *